United States Patent
Scott et al.

(10) Patent No.: US 9,103,756 B2
(45) Date of Patent: Aug. 11, 2015

(54) ALL-IN-ONE SAMPLE PREPARATION DEVICE AND METHOD

(71) Applicant: EMD Millipore Corporation, Billerica, MA (US)

(72) Inventors: Christopher A. Scott, Westford, MA (US); Timothy K. Nadler, Lexington, MA (US); Kurt Greenizen, Atkinson, NH (US); Louis Bonhomme, Waltham, MA (US); Sara D. Gutierrez, Danvers, MA (US); Masaharu Mabuchi, Beverly, MA (US); David Briggs, Douglas, MA (US); Phillip Clark, Wakefield, MA (US); Ralph T. Scaduto, Georgetown, MA (US)

(73) Assignee: EMD Millipore Corporation, Billerica, MA (US)

(*) Notice: Subject to any disclaimer, the term of this patent is extended or adjusted under 35 U.S.C. 154(b) by 120 days.

(21) Appl. No.: 14/031,458

(22) Filed: Sep. 19, 2013

(65) Prior Publication Data
US 2014/0017151 A1    Jan. 16, 2014

Related U.S. Application Data

(63) Continuation of application No. 13/534,570, filed on Jun. 27, 2012.

(60) Provisional application No. 61/507,240, filed on Jul. 13, 2011, provisional application No. 61/648,631, filed on May 18, 2012.

(51) Int. Cl.
*G01N 1/34* (2006.01)
*G01N 1/40* (2006.01)
(Continued)

(52) U.S. Cl.
CPC *G01N 1/34* (2013.01); *B01D 61/18* (2013.01); *B01D 63/06* (2013.01); *B01D 63/16* (2013.01);
(Continued)

(58) Field of Classification Search
CPC ..... B01L 3/5021; B01L 3/502; B01L 3/5085; B01L 2300/0618; B01L 2300/0681; B01D 61/18; B01D 61/20; B01D 63/06; B01D 63/16; B01D 2315/02; C07K 1/16; G01N 1/34; G01N 1/405; Y10T 436/25375; Y10T 436/255
See application file for complete search history.

(56) References Cited

U.S. PATENT DOCUMENTS

| 3,488,768 A | 1/1970 | Rigopulos |
| 4,190,530 A | 2/1980 | Forsythe, Jr. et al. |

(Continued)

FOREIGN PATENT DOCUMENTS

| EP | 0480298 A2 | 4/1992 |
| EP | 0865307 A1 | 9/1998 |

(Continued)

OTHER PUBLICATIONS

European Communication mailed Feb. 10, 2014 in corresponding European patent application No. EP 12175469.1.
(Continued)

*Primary Examiner* — Christopher A Hixson
(74) *Attorney, Agent, or Firm* — Nields, Lemack & Frame, LLC

(57) ABSTRACT

Sample preparation device that allows for a complete bind, wash, elute, buffer-exchange and concentration process to be carried out without sample transfer between multiple devices. The device includes a reservoir, a column for holding chromatography media, a holder region for holding a filtration device, and an outlet. The filtration device plugs into the holder region of the centrifugal device, and the assembly can be placed in an optional holder. The assembly, with or without the optional holder, can be placed in a conventional centrifuge tube for centrifugation. The entire bind, wash, elute, buffer exchange and concentration steps can be carried out with the apparatus without any pipette transfers (and the associated sample losses. The sample preparation device also can be used for binding and washing steps, in which case the filtration device is not needed, and for buffer exchange and concentration steps, in which case the media is not needed.

13 Claims, 28 Drawing Sheets

(51) Int. Cl.
| | |
|---|---|
| *B01L 3/00* | (2006.01) |
| *B01D 61/18* | (2006.01) |
| *B01D 63/06* | (2006.01) |
| *B01D 63/16* | (2006.01) |
| *C07K 1/22* | (2006.01) |
| *C07K 1/16* | (2006.01) |

(52) U.S. Cl.
CPC ............. *B01L 3/5021* (2013.01); *B01L 3/5085* (2013.01); *C07K 1/16* (2013.01); *C07K 1/22* (2013.01); *G01N 1/405* (2013.01); *B01D 2315/02* (2013.01); *B01L 2300/0618* (2013.01); *B01L 2300/0681* (2013.01); *Y10T 436/25375* (2015.01)

(56) References Cited

U.S. PATENT DOCUMENTS

| | | | |
|---|---|---|---|
| 4,632,761 | A | 12/1986 | Bowers et al. |
| 4,722,792 | A | 2/1988 | Miyagi et al. |
| 4,769,145 | A | 9/1988 | Nakajima |
| 4,956,298 | A | 9/1990 | Diekmann |
| 5,484,572 | A | 1/1996 | Katakura et al. |
| 5,552,325 | A | 9/1996 | Nochumson et al. |
| 5,601,711 | A | 2/1997 | Sklar et al. |
| 5,647,990 | A | 7/1997 | Vassarotti |
| 5,833,860 | A | 11/1998 | Kopaciewicz et al. |
| 5,882,943 | A | 3/1999 | Aldeen |
| 6,156,199 | A | 12/2000 | Zuk, Jr. |
| 6,171,869 | B1 | 1/2001 | Safarian et al. |
| 6,269,957 | B1 | 8/2001 | Bowers et al. |
| 6,344,140 | B1 | 2/2002 | Zuk, Jr. |
| 6,355,792 | B1 | 3/2002 | Michelsen et al. |
| 6,368,800 | B1 | 4/2002 | Smith et al. |
| 6,375,855 | B1 | 4/2002 | Vassarotti |
| 6,673,631 | B1 | 1/2004 | Tereba et al. |
| 6,699,987 | B2 | 3/2004 | Hillebrand et al. |
| 6,719,896 | B1 | 4/2004 | Clark |
| 6,837,995 | B1 | 1/2005 | Vassarotti et al. |
| 6,919,200 | B2 | 7/2005 | Ibrahim |
| 7,045,064 | B2 | 5/2006 | Warner |
| 7,767,804 | B2 | 8/2010 | Bair, Jr. et al. |
| 8,062,533 | B2 | 11/2011 | Dawson |
| 8,187,476 | B2 | 5/2012 | Dawson |
| 8,357,296 | B2 | 1/2013 | Bonhomme et al. |
| 8,747,670 | B2 | 6/2014 | Bonhomme et al. |
| 2002/0102563 | A1 | 8/2002 | Gjerde et al. |
| 2005/0254995 | A1 | 11/2005 | Sostek et al. |
| 2007/0215554 | A1 | 9/2007 | Kreuwel et al. |
| 2009/0078638 | A1 | 3/2009 | Bonhomme et al. |
| 2012/0214974 | A1 | 8/2012 | Dawson |
| 2013/0017620 | A1 | 1/2013 | Scott et al. |
| 2013/0032539 | A1 | 2/2013 | Bonhomme et al. |
| 2013/0186830 | A1 | 7/2013 | Bonhomme et al. |
| 2014/0224723 | A1 | 8/2014 | Bonhomme et al. |

FOREIGN PATENT DOCUMENTS

| | | |
|---|---|---|
| EP | 1621890 A1 | 2/2006 |
| GB | 2378445 A | 2/2003 |
| JP | 50-22509 B | 7/1975 |
| JP | 54-136469 A | 10/1979 |
| JP | 62-176560 A | 8/1987 |
| JP | 1-297161 A | 11/1989 |
| JP | 2-1255 U | 1/1990 |
| JP | 5-192608 A | 8/1993 |
| JP | 7-103971 A | 4/1995 |
| JP | 8-501727 A | 2/1996 |
| JP | 2001-95572 A | 4/2001 |
| JP | 2004-517310 A | 6/2004 |
| JP | 2010-540927 A | 12/2010 |
| TW | 215416 B | 11/1993 |
| TW | 274132 B | 4/1996 |
| TW | 281915 B | 7/1996 |
| WO | 93/16801 A1 | 9/1993 |
| WO | 93/24213 A1 | 12/1993 |
| WO | 95/30484 A1 | 11/1995 |
| WO | 97/21484 A1 | 6/1997 |
| WO | 97/43641 A1 | 11/1997 |
| WO | 99/09042 A2 | 2/1999 |
| WO | 00/48716 A2 | 8/2000 |
| WO | 01/42487 A2 | 6/2001 |
| WO | 02/26364 A2 | 4/2002 |
| WO | 02/053256 A1 | 7/2002 |
| WO | 2005/012521 A1 | 2/2005 |
| WO | 2007/140417 A2 | 12/2007 |
| WO | 2008/043551 A1 | 4/2008 |
| WO | 2009/042023 A1 | 4/2009 |

OTHER PUBLICATIONS

Notice of Allowance mailed Feb. 3, 2014 in co-pending U.S. Appl. No. 13/649,365.

Amicon Ultra Article, Millipore Corporation protocol note, "Urine Concentration Prior to Agarose Gel Electrophoresis and Immunofixation Electrophoresis", Jul. 2002, 2 pages.

International Search Report/Written Opinion mailed Nov. 20, 2008 in co-pending PCT application No. PCT/US08/10145.

Extended European Search Report dated Jul. 28, 2011 in co-pending foreign patent application No. EP 08795626.4.

Japanese Communication, with English translation, mailed May 22, 2012 in co-pending Japanese patent application No. JP 2010-526890.

Japanese Communication, with English translation, mailed Jul. 16, 2013 in corresponding Japanese patent application No. JP 2012-157783.

Office Action-Restriction-mailed Dec. 26, 2012 in co-pending U.S. Appl. No. 13/649,365.

Office Action mailed Jan. 23, 2013 in co-pending U.S. Appl. No. 13/649,365.

Final Rejection mailed Apr. 19, 2013 in co-pending U.S. Appl. No. 13/649,365.

Notice of Allowance mailed Apr. 7, 2015 in co-pending U.S. Appl No. 13/739,008.

Office Action mailed Apr. 9, 2015 in corresponding U.S. Appl. No. 13/534,570.

English translation of Taiwanese communication mailed Apr. 7, 2015 (including attached original and reissued Search Report) in corresponding Taiwanese patent application No. 101124894.

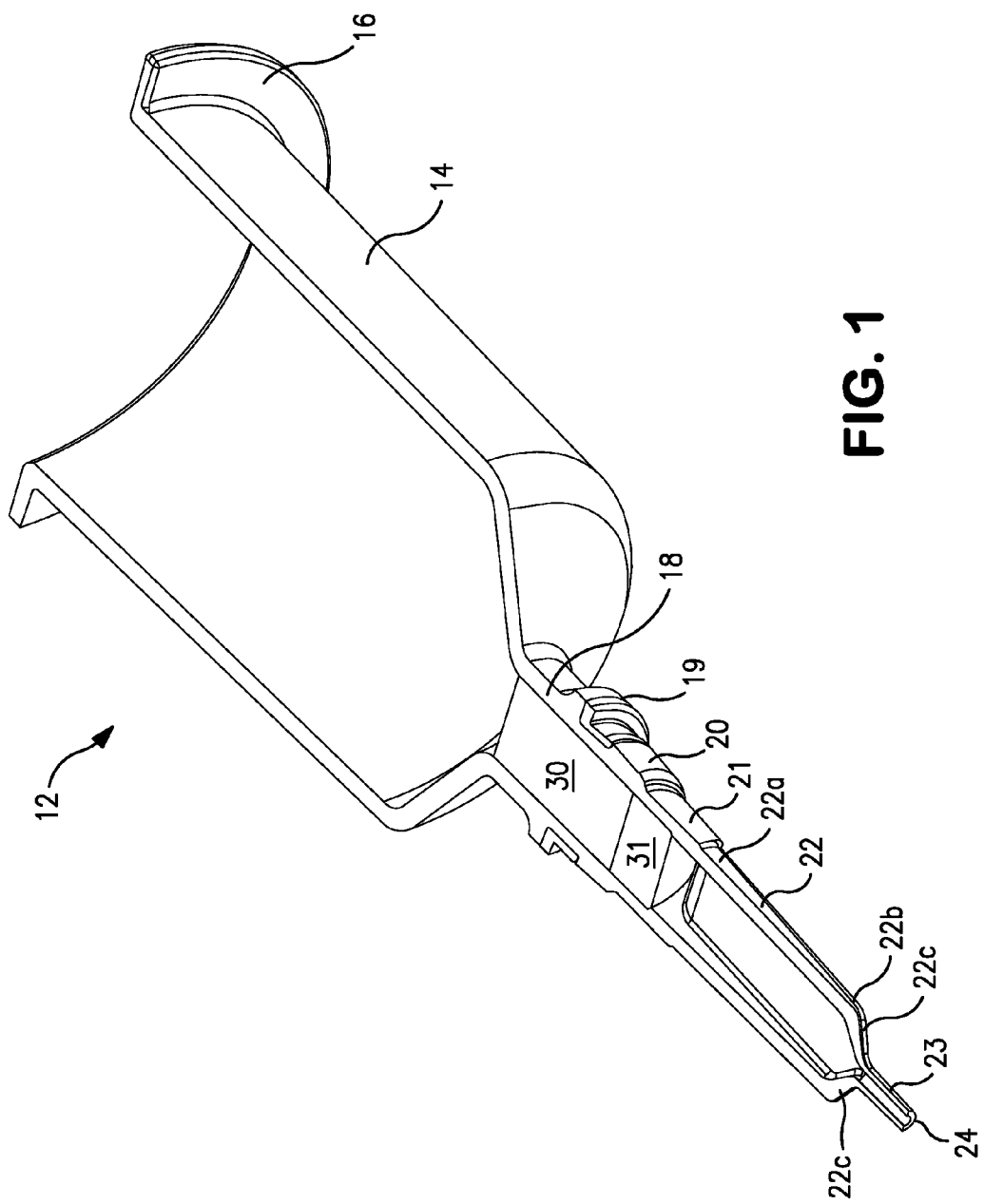

ALL-IN-ONE SAMPLE PREPARATION DEVICE AND METHOD

This application is a Continuation of U.S. patent application Ser. No. 13/534,570 filed Jun. 27, 2012, which claims priority of U.S. Provisional Application Ser. No. 61/507,240 filed Jul. 13, 2011 and U.S. Provisional Application Ser. No. 61/648,631 filed May 18, 2012, the disclosures of which are incorporated herein by reference.

BACKGROUND

Centrifugal filters may be used to separate biological substances such as an antibody enzyme, nucleic acid and protein for the purpose of concentration, desalting, purification, and fractionation. These devices are most commonly used in centrifugal-separator instruments, which may consist of a fixed-angle-rotor configuration or a swing- or variable-angle-rotor configuration. The speed of the filtering process and the recovery of retentate sample are highly valued by customers. Sample recovery values higher than 85% are usually obtained by removing the membrane capsule (sample holder) and reverse spinning it in a receiver tube.

Such devices are typically used to concentrate urine, serum, plasma and cerebrospinal fluid. For example, the measurement of specific proteins in urine can be important for the diagnosis and management of various disease states, yet the content of these proteins in urine is often too small to be detected without first concentrating the proteins. Conventional devices generally include a housing having a sample reservoir, a filter sealed in the housing so that the sample must past through the filter when subject to a driving force (such as centrifugation), and a collection chamber for collecting the concentrated sample.

There is a class of protein purification protocols that use antigen-protein affinity to separate proteins of interest from a mixed sample such as a cell lysate or serum. Such protocols often use small beads that are conjugated with antibodies such that they bind to specific proteins from the sample. Once the proteins are effectively bound to the beads, there is a need to extract and collect the proteins (elution) from the beads for downstream analysis, assay development, etc. Exemplary downstream analysis techniques include 2D gel electrophoresis and mass spectrometry.

There are a number of processing steps that are needed in the workflow. These can include equilibrating the beads with neutral buffer prior to binding, washing the beads after binding to remove unbound contaminates, eluting the proteins of interest, exchanging the buffer from the eluted proteins, concentrating the final diluted sample, and finally recovering the purified proteins sample. For affinity purification and immunoprecipitation protocols, the proteins bound to the beads are the proteins of interest. For depletion protocols, the unbound fraction (proteins not bound to the beads) is the sample of interest.

Beads used in these purification methods are magnetic or non-magnetic. One of the most common non-magnetic beads is agarose. Magnetic beads such as PureProteome protein A & G, PureProteome albumin and PureProteome albumin and IgG for albumen and IgG depletion from serum, Magna ChIP protein A beads for chromatic immuniprecipitation, and PureProteome Nickel magnetic beads for His-tagged recombinant purification, are commercially available from EMD Millipore.

When working with magnetic beads, current manual methods rely on the use of pipettes to move liquids to and from the sample tube (buffers, etc.) and to move the sample from one device to another. Magnets are used to hold the beads to the side of the sample tube so that the user can pipette out the buffers without disturbing the beads. There are about 8 pipette steps per sample in a typical bind/wash/elute workflow.

For optimal protein binding with the beads, incubation is required with these methods. The device containing the beads and the sample are usually turned in an end-over-end mixer, or placed in a shaker (e.g., vortexor) for 10-30 minutes. When new buffers are added, such as wash and elution buffers, the user will vortex the device for a minute or so to mix and wash.

The washing and eluting steps need to be repeated multiple times in order to be effective. For example, standard protocol is to add wash buffer to the sample vial, vortex (mix) for a minute or so, remove the buffer and repeat two or more times. With magnetic beads, the bind/wash/elute procedure takes about 45 minutes.

An alternative to magnetic beads is agarose beads. One commercially available device that uses agarose beads includes a tube with an open bottom and a porous frit positioned over the open bottom. Instead of using pipettes to remove fluids from the sample tube, a bench top centrifuge is used to drive the fluids through the frit and into a collection tube—typically a 4 mL or 15 mL tube. The frit pore size is chosen to retain the beads while allowing buffers and proteins to pass through.

Depending on the size of the spin column used, the workflow can be cumbersome and time consuming compared to methods that use magnetic beads. A bench top centrifuge is typically a shared piece of equipment located at a common location; unlike microcentrifuges that each user may have setup at their work area.

This process requires 16 pipetting steps per sample and takes about 1 hour to complete.

For both magnetic and agarose workflows, downstream steps may include exchanging the carrier buffer and concentrating a diluted sample. In cases where buffer exchange of the sample is desired, perhaps to remove the eluent like imidazole, the sample is typically transferred to a dialyzing membrane tube with clamps or the like, which is then placed inside a tank of exchange buffer for up to 24 hours as the buffer is exchanged gradually by way of diffusion.

Where buffer exchange and concentration is desired, a diafiltration/protein concentration device can be used, such as a centrifugal device with a porous UF membrane sized to retain the proteins, but allow the buffer to pass through. By controlling the spin time and selecting an appropriate device design, the final concentration can be controlled. For the buffer exchange to be effective, the buffer exchange step needs to be repeated two or three times (like was done with the wash and elution steps). These devices take 30-45 minutes and require multiple spins in a centrifuge. In the Amicon Ultra device commercially available from EMD Millipore, there are 5 pipette steps for buffer exchange and concentration.

As the volumes of protein samples become smaller, the undesirable potential losses of samples due to the hold-up volume within a device have become more important than ever. Current data suggest that 10 μL loss in a concentrated sample of 50 μL represents 80% protein recovery. If the protein loss were reduced by one order of magnitude from 10 μL to 1 μm, protein sample recoveries could be increased from 80% to 98%. An 18% improvement in protein sample recovery could be very valuable.

It would be desirable to provide a device and method that efficiently and effectively performs a bind and wash, a buffer exchange and concentration, and/or a complete bind, wash and elute, buffer exchange and concentration in a single device without the need to pipette transfer the precious sample between devices, particularly for sample sizes up to about 11 mL.

SUMMARY

The problems of the prior art have been overcome by the embodiments disclosed herein, which in certain embodiments includes a sample preparation device that allows for a bind and wash, a buffer exchange and concentration, and/or a complete bind, wash, elute, buffer-exchange and concentration process to be carried out without sample transfer between multiple devices. In accordance with certain embodiments, a centrifugal device is provided that includes a reservoir having an inlet, a column for holding media such as a bed of packed beads, a holder region for receiving in sealing relation a filtration device, and an outlet. In accordance with certain embodiments, the filtration device includes a housing having a sample reservoir, one or more, preferably two, substantially vertically oriented membranes (spaced apart where more than one is present) disposed in the housing, an underdrain associated with each membrane such that fluid passing through each membrane flows through a respective underdrain into a filtrate collection chamber. The filtration device plugs into the holder region of the centrifugal device, and the assembly can be placed in an optional holder. The assembly, with or without the optional holder, can be placed in a conventional centrifuge tube for centrifugation. The entire bind, wash, elute, buffer exchange and concentration steps can be carried out with the apparatus without any pipette transfers (and the associated sample losses), resulting in superior sample of interest recovery. The sample preparation device also can be used for binding and washing steps, in which case the filtration device is not needed, and for buffer exchange and concentration steps, in which case the media is not needed. Multiple buffer exchanges can be carried out in the same device.

In accordance with certain embodiments, the device can include a retractable feeder tube, such as to help reduce the loss of sample solutions that accumulate on the inner wetted bore and exterior surface of the feeder tube.

In accordance with certain embodiments, a sample is incubated with the media in place in the device so that the selected target binds to the media. The remaining unbound sample then can be washed away. The sample is purified by eluting the target sample of interest from the media by adding a buffer that causes the media to release the captured target back into solution. Once a sample is purified, it can be concentrated to a useful concentration for analysis or storage (most proteins are most stable when stored at a concentration near 1 mg/ml).

In accordance with certain embodiments, the sample preparation device can include a biasing member or diaphragm that can be actuated to evacuate small values (e.g., hold-up volumes) of sample from the device.

The sample preparation device results in overall time savings for bind and wash, buffer exchange, and/or bind, wash, elute and concentration protocols. No sample pipetting is required, resulting in higher sample recovery. Buffer exchange can be carried out in substantially less time than previously possible, with a single centrifuge spin step for each of buffer exchange and wash steps rather than multiple spin steps previously required. No binding incubation period is necessary.

In accordance with certain embodiments, the assembly interface between the filtration device and the exchange chamber can allow relative movement or separation such as by mechanical means such as a physical stop or by self actuating geometry subject to centrifugal pressure gradient to remove tip engagement with captured target to optimize sample recovery.

Advantages achieved with the devices and methods disclosed include but are not limited to shortened incubation times for affinity separation processes; improved sample concentration in one device platform; improved sample recovery using invert spinning out centrifugal devices; and single spin buffer exchange dilutions.

BRIEF DESCRIPTION OF THE DRAWINGS

FIG. 1 is a perspective view, in cross-section, of a reservoir/exchange member in accordance with certain embodiments;

DETAILED DESCRIPTION OF THE INVENTION

Figure 1B:
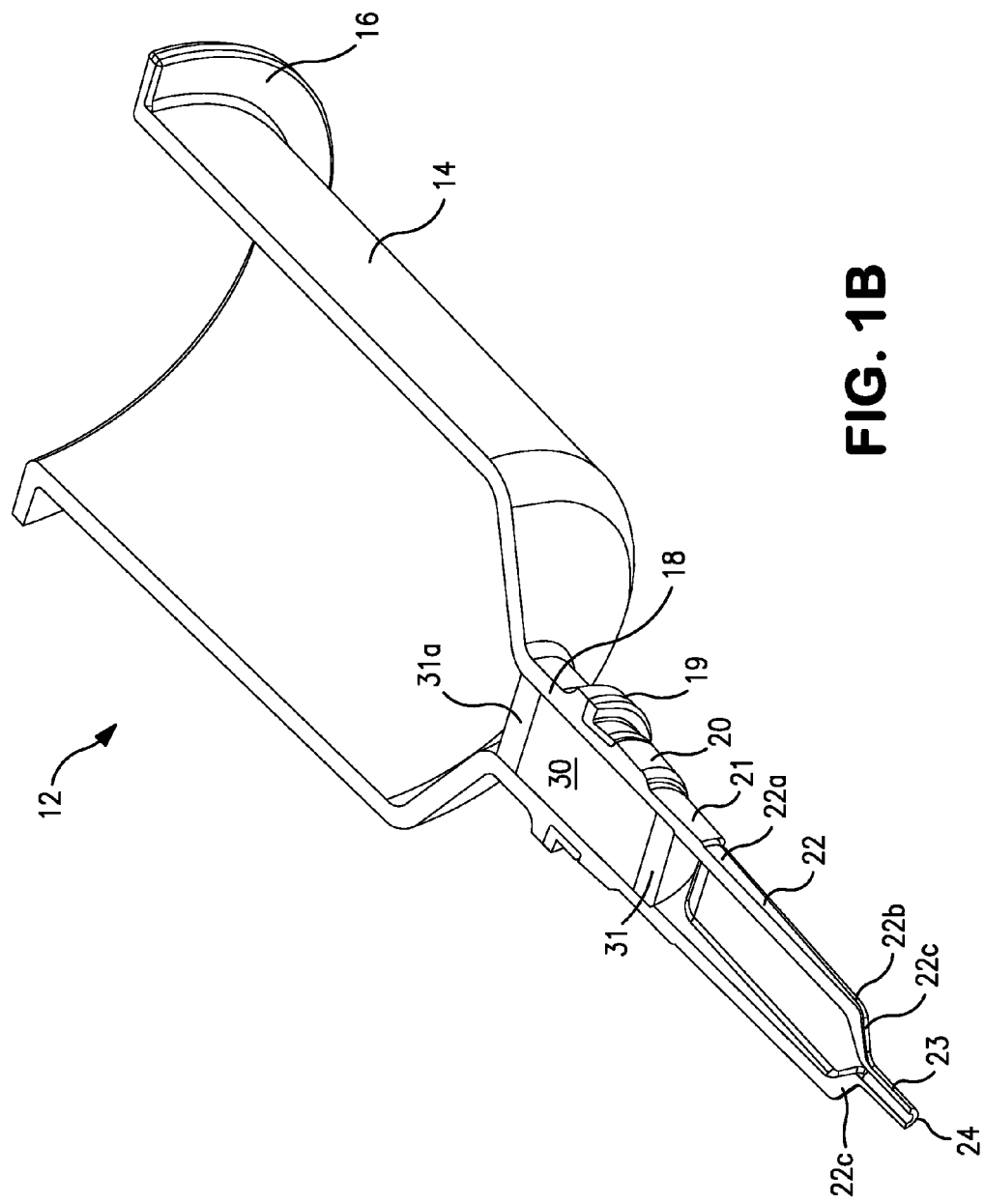
FIG. 1B is a perspective view, in cross-section, of a reservoir/exchange member containing a pre-packed bead column in accordance with certain embodiments.

Turning first to FIG. 1, there is shown a reservoir/exchange member 12 in accordance with certain embodiments. The member 12 is preferably made of a low binding, clear material capable of withstanding the forces typically encountered during centrifugation. Suitable materials include clarified polypropylene or polycarbonate. In certain embodiments the member 12 includes a generally cylindrical sample reservoir 14 having an open top (inlet), although other shapes are suitable and within the scope of the embodiments disclosed herein. A top annular flange 16 having an outside diameter larger than the outside diameter of the reservoir 14 can be provided which can seat in a centrifuge tube cap (not shown in FIG. 1). The volume or capacity of the reservoir 14 is not particularly limited, and can be chosen based upon the sample size and/or the size of the filtration device to which the reservoir is to be connected. Exemplary volumes include 3 ml and 11 ml. In certain embodiments, the bottom of the reservoir 14 is frusto-conical shaped, tapering downwardly (in the direction of fluid flow from the open top) and radially inwardly, converging to a central opening which leads to a column 18 of lesser diameter than that of the reservoir 14. The upper portion of the column 18 has a diameter and length chosen to hold a sufficient amount of media to carry out a binding step, and is thus positioned downstream, in the direction of sample flow during a binding operation, of the sample reservoir 14. In embodiments where no binding is desired (e.g., a buffer exchange and concentration protocol), the media can be omitted from the column 18. Preferably the column diameter and length are sufficient to hold at least 200 microliters of beads, creating a packed bed. An exemplary diameter is about ¼ inch, with a length of ¼ inch or more. Where media is used, a media retaining structure such as a porous frit 31 can be placed below the media 20 to hold the media in place, in the case of a pre-packed column the need would exist for an additional retaining structure 31a positioned above the media to contain the media within the column diameter (FIG. 1B). The column 18 can include an annular flange 19, which provides a shoulder or stop against which the filtration device 50 is positioned during use (e.g., with an interposed gasket 40 (FIG. 2), providing a liquid sealing interface between the filtration device 50 and the member 12). Below the annular flange 19, the column has a holder region 20 of intermediate diameter, which is received in the upper portion of the sample reservoir of the filtration device when positioned on the column during use. The region 20 has an outside diameter less than the outside diameter of the annular flange 19. A downstream further stepped down diameter portion 21, having an outside diameter less than the outside diameter of region 20, sits in a lower region of the sample reservoir portion of the filtration device, above the membranes, when positioned on the column during use.

The region 22 of the column 18 has a finned geometry, tapering radially from a relatively thick upper portion 22a to a relatively thin lower portion 22b, and defines a bind/elute chamber. At the thinner portion 22b, the column tapers radially inwardly at 22c, converging in a stem 23, preferably centrally located, that has an open bottom end 24, the stem extending axially from the finned-shaped column. The finned feature is shaped to fit inside of the mating filtration device 50 with the inside cored out to maintain a uniform wall thickness. In accordance with certain embodiments, the finned feature allows the region 22 of the column 18 to occupy substantially the entire volume between the membranes 12A and 12B of the filtration device 50, thereby maintaining the desired sample volume near the open bottom end 24. Preferably the stem is cylindrical and tapers radially inwardly towards the open bottom end 24. The open bottom end 24 allows for fluid communication between the reservoir 14 (through any media and frit present, and through the region 22 (bind/elute chamber)) and a downstream device such as a tube or a filtration device.

In accordance with certain embodiments, the media can be chromatography media, such as media used to capture selected analytes in a sample and release them when the buffer conditions are appropriately changed. Suitable media includes beads that bind metal chelate, protein A, glutathione, albumin, etc. The media may be magnetic, non-magnetic, agarose, etc., and may be modified with certain chemistries such as IMAC, protein A, glutathione, streptavidin, etc. Accordingly, the media can include appropriate chemistries to effectuate the desired binding.

Figure 23:
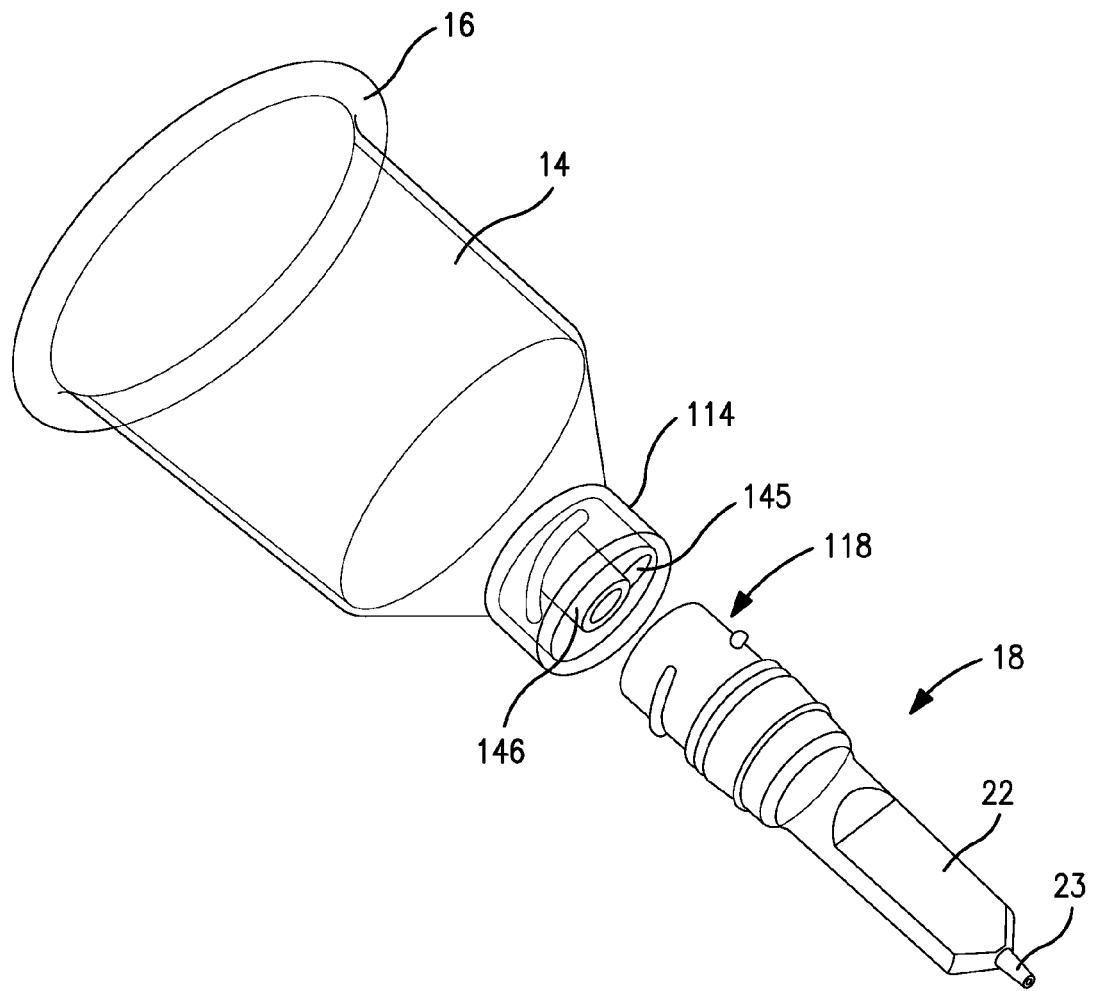
FIG. 23 is a perspective view of a reservoir-exchange device in accordance with a first alternative embodiment.
Figure 24:
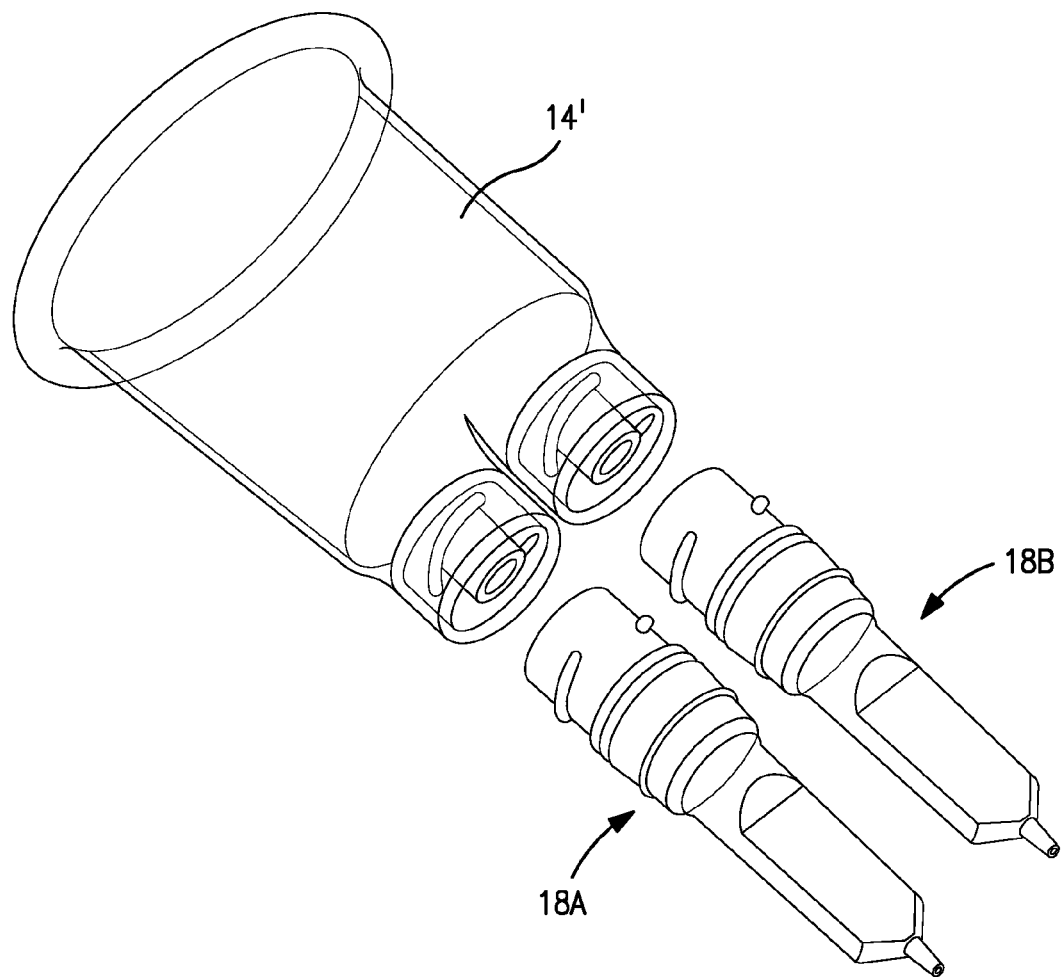
FIG. 24 is a perspective view of a reservoir-exchange device in accordance with a second alternative embodiment.
Figure 25:
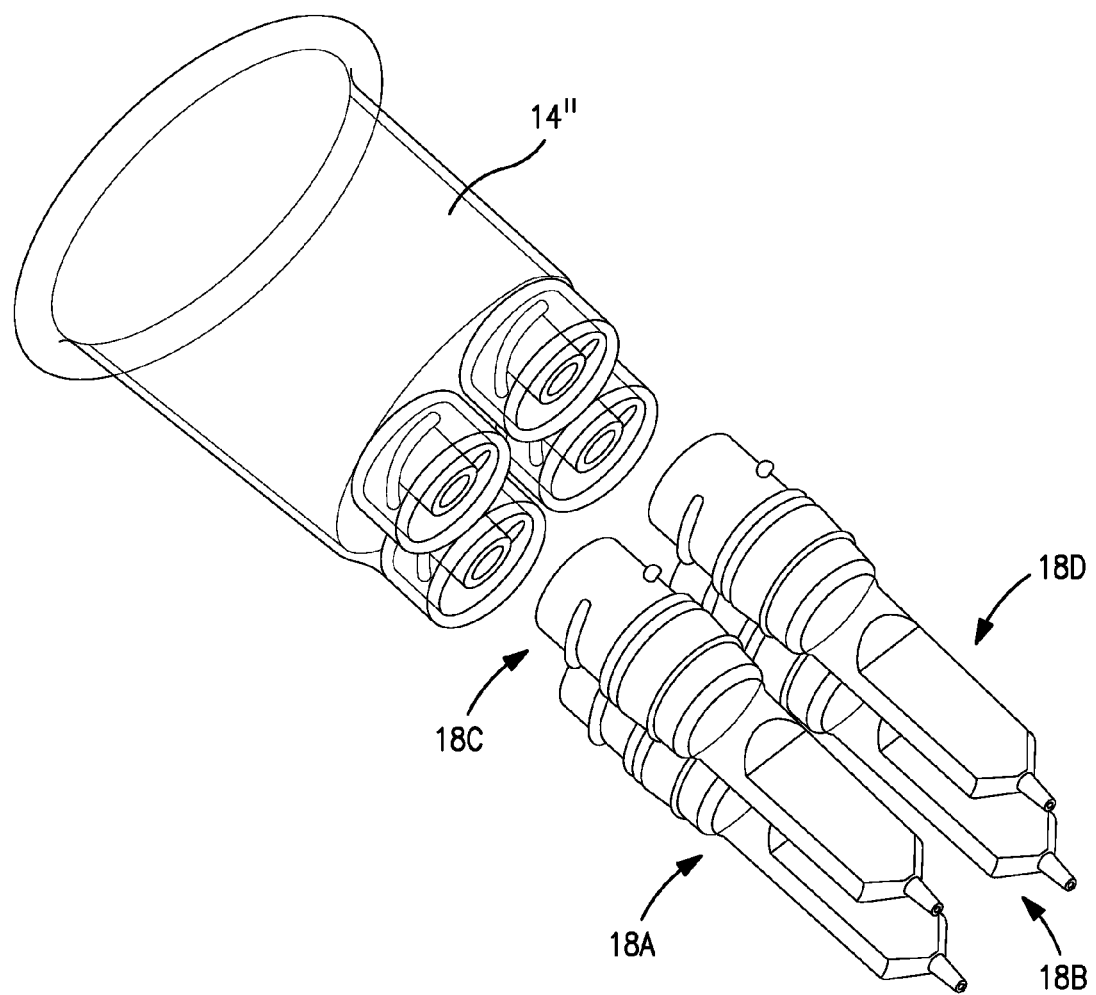
FIG. 25 is a perspective view of a reservoir-exchange device in accordance with a third alternative embodiment.

In accordance with certain embodiments, the finned lower portion and column can form a single detachable feature that can be attached to the reservoir 14 such as by a snap fit, luer fit, screw on, etc. The detachable feature reduces the amount of plastic waste and the cost of the disposable, as the reservoir portion can be washable and reusable. An exemplary device where the column 18 is removable is shown in FIG. 23. Although any suitable connection mechanism can be used to connect the column 18 to the reservoir 14, FIG. 23 shows an embodiment wherein the column 18 includes a threaded portion 118 that is threadingly received in the lower portion 144 of the reservoir 14 that contains internal grooves 145 that mate with the threads on the threaded portion 118. Lower portion 114 is preferably cylindrical and circumscribes spout 146 that is in fluid communication with the reservoir 14. The removability of the column 18 allows flexibility in using different columns 18 with the same reservoir 14. FIGS. 24 and 25 show similar embodiments where multiple columns can be attached to the reservoir. For example, reservoir 14' in the embodiment of FIG. 24 has two outlets, and two removable columns 18A and 18B can be attached, each to a respective outlet. Similarly, reservoir 14" in the embodiment of FIG. 25 has four outlets, and four removable columns 18A, 18B, 18C, and 18D can be attached, each to a respective outlet.

Figure 2:
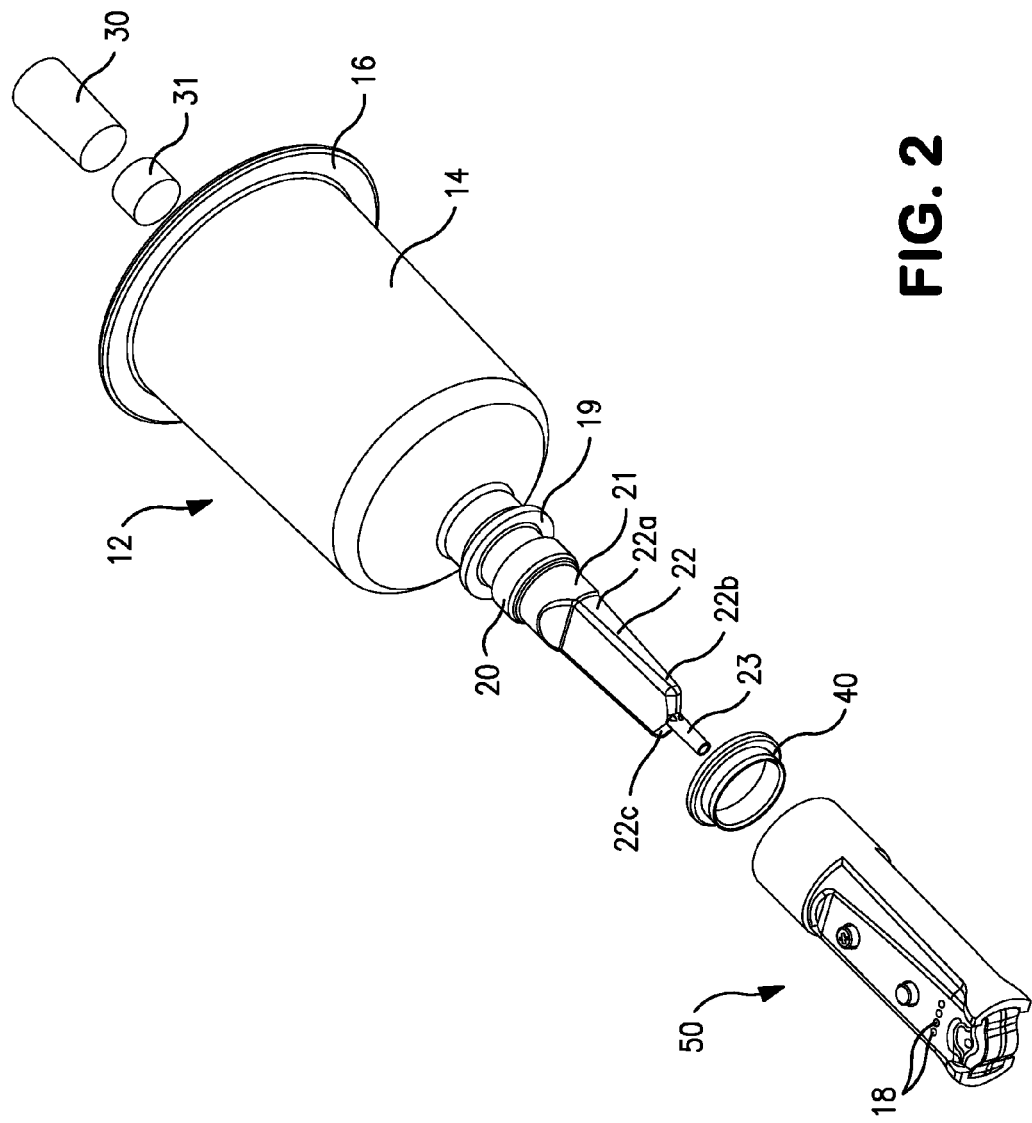
FIG. 2 is an exploded view of a reservoir/exchange member and filtration device in accordance with certain embodiments.

FIG. 2 is an exploded view of the member 12 and filtration device 50, with the filtration device 50 shown oriented to be received by the column 18 of the member 12. In view of the flattened and tapered configuration of the region 22 of the column 18, and in view of the symmetry of the filtration device 50, the filtration device 50 can only fit on the column 18 in one of two ways; that shown in FIG. 2, and that 180° rotated therefrom. In the embodiment shown, a gasket 40 is used to provide a liquid tight seal between the filtration device 50 and the member 12. Other sealing mechanism can be used, such as O-rings or custom shaped overmolded seals including face seals, flexible reed type seals, etc. Such overmolded seals can be integrally molded.

Figure 3:
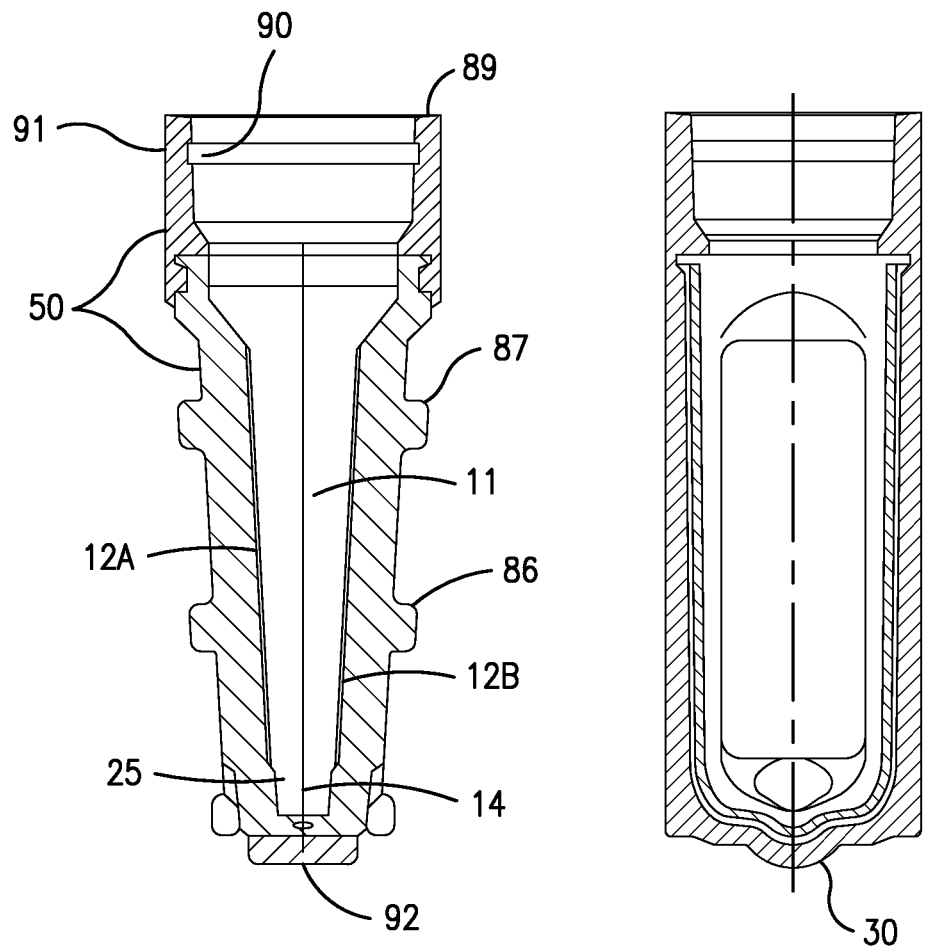
FIG. 3 is a vertical oriented, cross-sectional side view of a filtration device in accordance with certain embodiments.

Turning now to FIG. 3, there is shown a filtration device 50 suitable for use in accordance with certain embodiments. The filtration device 50 is that described in U.S. Publ. No. 2009/0078638, the disclosure of which is hereby incorporated by reference. The device 50 includes a sample reservoir 11 to receive an unfiltered sample, and first and second membranes 12A and 12B each arranged on a side wall of the device 50 as shown. A retentate chamber 14 defining a dead-stop volume is provided below the membranes 12A and 12B. A collection tip 30 that is generally arc-shaped and protrudes outwardly from the bottom perimeter of the device may be provided to localize the dead-stop volume at the centerline of the device, and subsequently reduce variability of the dead-stop volume as the angle of orientation in a centrifuge changes. Preferably the device 50 is made of a solid material that is liquid impermeable, has low protein binding characteristics, and is sufficiently strong to withstand the gravitational forces (Gs) applied during centrifugation. Suitable materials include acrylic, CYROLITE G20 HiFlo resin, ESTAR HN631 resin and KRATON polymers. The side panels in particular can be made of a clear plastic material which enables an operator or user to see into the interior cavity of the device so as to determine the fluid levels prior to, and after the filtration process. The side panels each include an underdrain support that supports the membrane and provides fluid communication to the retentate chamber 14. For example, the underdrain support can include a series of spaced longitudinal grooves, channels, or surface textures that are located beneath the membrane to capture filtrate as it passes through the membrane and direct it towards the drain holes and into a receiver vial. Each membrane is sealed to a respective side panel so that only fluid passing through the membrane can exit the drain holes of the device located in the side panels. In certain embodiments, each membrane 12A, 12B is coextensive with a respective underdrain support and is sealed thereto. The geometry of the underdrain is intended to support the membrane and keep it as flat as possible, while allowing sufficient open space underneath the membrane to enable fluid to flow and pass through the drain holes 18 of the device. It is preferred that hydraulic fluid resistance be kept as low as possible.

Suitable membranes include microporous and ultraporous membranes, the latter being useful for ultrafiltration. Regenerated cellulose ultrafiltration membranes (e.g., "Ultracel Amicon YM" and "Ultracel PL" membranes available from Millipore Corporation of Bedford, Mass.) are well-suited for devices targeted for concentrating or desalting extremely dilute or hydrophobic sample liquids. The use of a hydrophilic membrane having a "tight" microstructure promotes good retention with low adsorption of protein, DNA, and other macromolecules. Polyethersulfone ultrafiltration membranes (e.g., "Amicon PM" and "Biomax PB" also available from Millipore Corporation), or other like membrane having an "open" microstructure suitable for rapid separation, are better-suited for devices targeted for concentrating and desalting more concentrated sample liquids, such as serum, plasma, and conditioned tissue culture.

Preferably each membrane 12A, 12B is oriented at a slight angle with respect to the longitudinal centerline of the device 10, such that the top of each membrane is spaced from the longitudinal centerline a distance greater than the bottom of the membrane. A funnel-shaped configuration is formed. So positioning each membrane takes advantage of tangential flow effects during centrifugation. An angle greater than about 0° and less than about 5°, preferably about 3°, has been found to be suitable.

The side panels each include one or more drain holes 18 (FIG. 2) that are in fluid communication with the retentate chamber 14 and enable filtrate to pass through the device housing for collection in another housing. Each drain hole 18 is preferably located at the bottom of a respective underdrain groove or channel and is preferably substantially circular in cross-section. The drain holes should be located a sufficient distance from the side edges of the panels so that the holes are not constricted or otherwise deleteriously altered during a heat seal operation that can be used during manufacture of the device. Preferably the drain holes 18 are equally spaced from one another and are co-linear.

Figure 4:
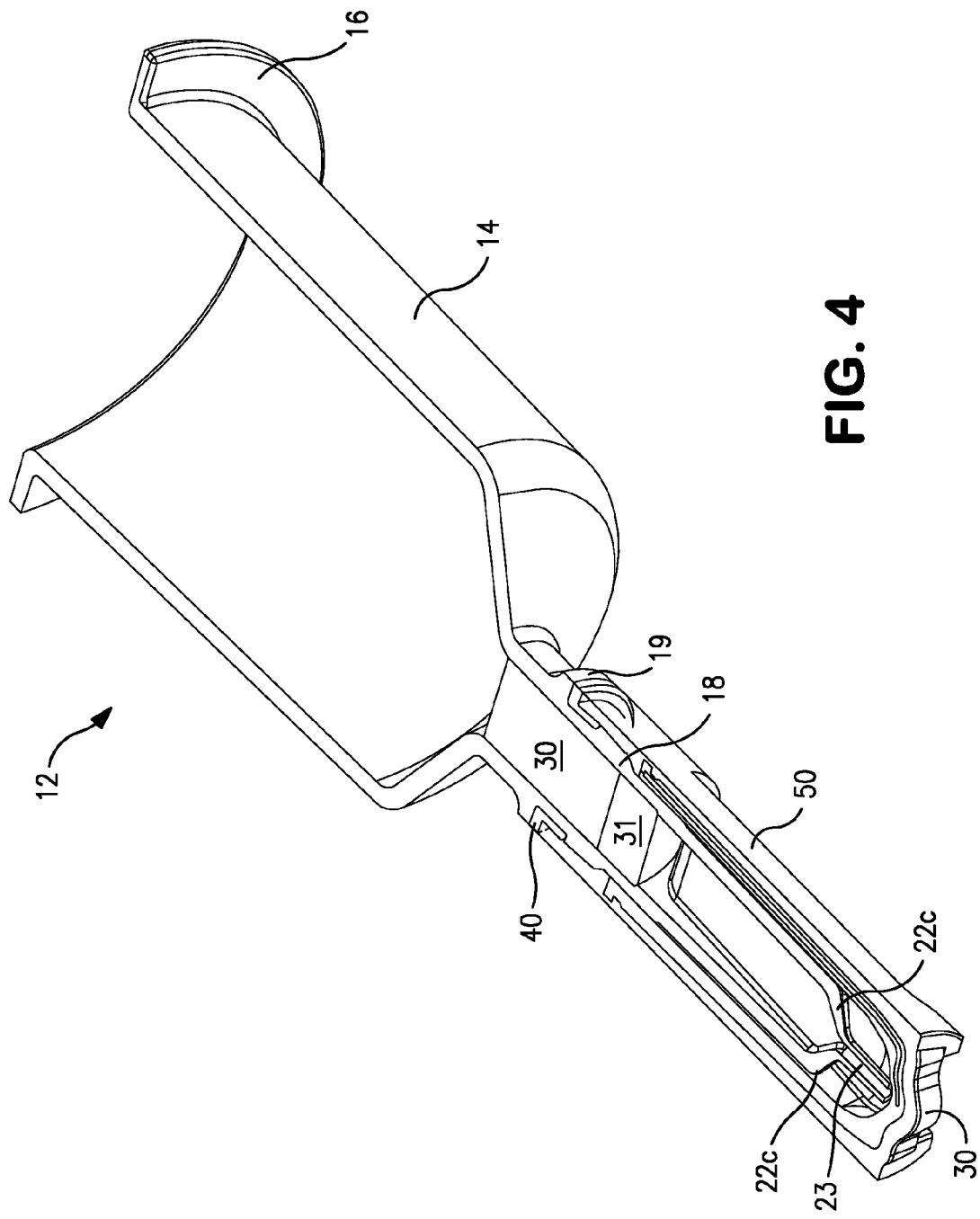
FIG. 4 is a perspective view, in cross-section, of a reservoir/exchange member and a filtration device positioned therein in accordance with certain embodiments.

FIG. 4 shows the member 12 with a filtration device 50 positioned in place on the column 18 of the member 12 in accordance with certain embodiments. The gasket 40 can be seen providing a sealing interface between the filtration device 50 and the flange 19 of the column 18. Preferably the stem 23 of the member 12 is positioned to be within the deadstop volume of the filtration device 50, as discussed in greater detail below.

Figure 5:
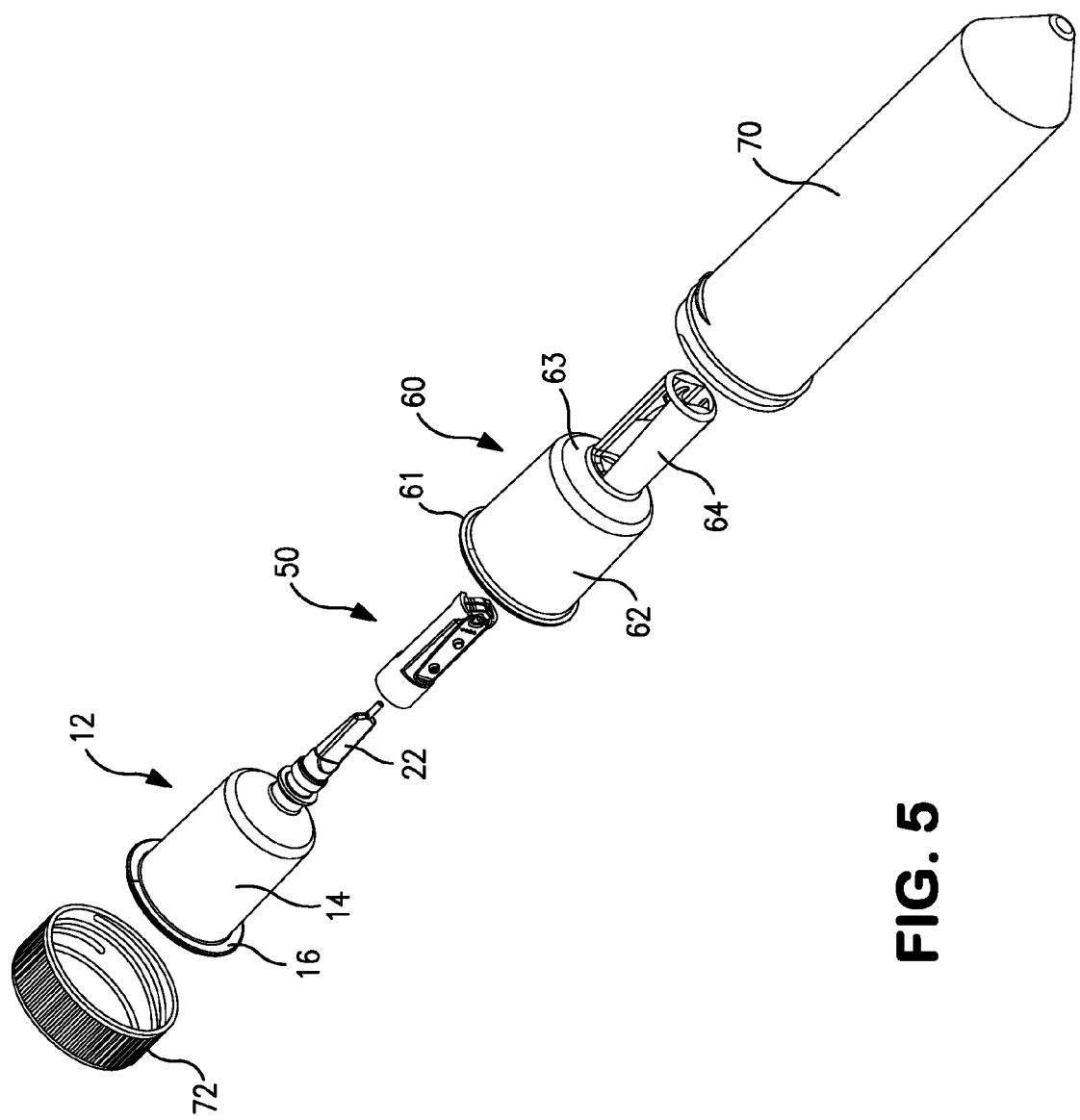
FIG. 5 is an exploded view of a reservoir/exchange member, filtration device, optional assembly holder, centrifuge tube and cap in accordance with certain embodiments.
Figure 6:
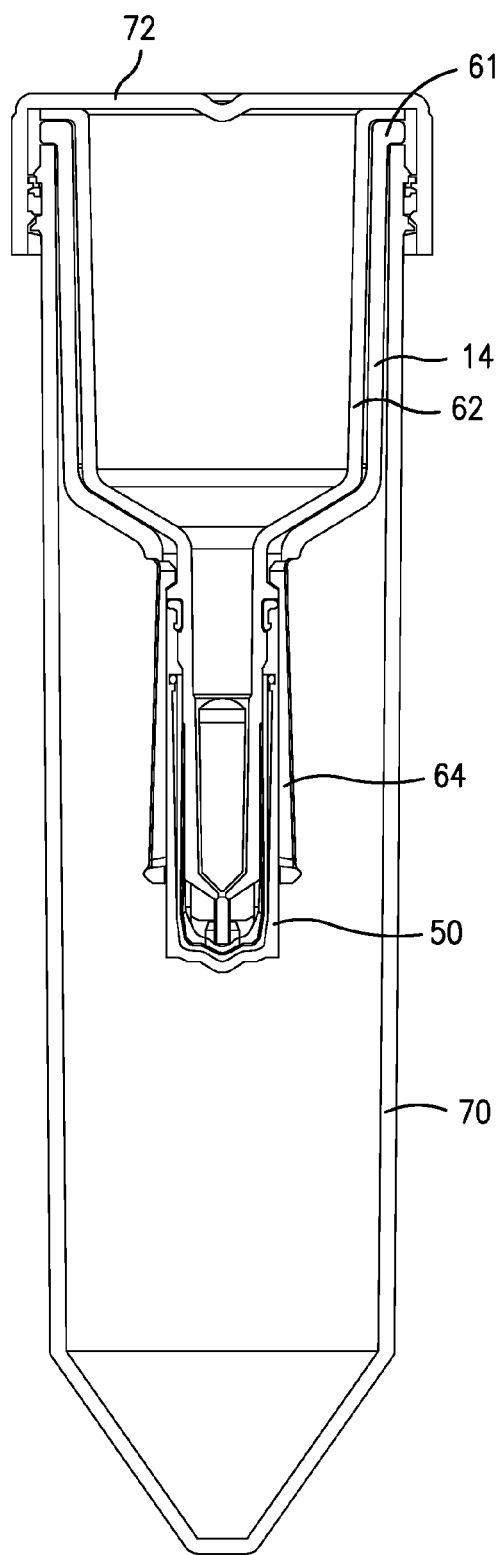
FIG. 6 is a cross-sectional view of an assembly including a reservoir/exchange member, filtration device, assembly holder, centrifuge tube and cap in accordance with certain embodiments.

As seen in FIG. 5, in accordance with certain embodiments, an optional assembly holder 60 can be provided where maintaining the member 12 attached to the filtration device 50 is a concern under the centrifugal forces typically applied to the assembly. In certain embodiments, the holder 60 can be made of the same material as the member 12, and includes a cylindrical top retention sleeve 62 configured to receive the reservoir 14 of the member 12. A top annular flange 6 extending radially outwardly provides a seat for the annular flange 16 of the member 12. In accordance with certain embodiments, the bottom 63 of the retention sleeve 62 is frusto-conically shaped to receive the similarly shaped bottom of the reservoir 14. A centrally located aperture in the bottom 63 leads to an axially extending cylindrical column 64 having a bore. The bore is shaped to receive filtration device 50, such that a lower portion of the filtration device 50 protrudes axially out the bore (FIG. 6).

To assemble the components such as for centrifugation, the filtration device 50 can be inserted onto the column 18 of the member 12, and then can be inserted into the holder 60. The combination is then placed in a conventional centrifuge tube 70 (e.g., 15 or 50 ml), having a outside diameter such that the flange 61 sits on the top surface of the tube 70 (FIG. 6). Cap 72 then can be screwed onto the tube or otherwise connected to secure the assembly in the tube. Where the optional holder 60 is omitted, the flange 16 of the member 12 sits on the top surface of the tube 70.

For most purification and IP protocols, the bind and wash steps can be carried out with the filtration device detached from the column 22. The filtration device can then be attached to the column 22 and proteins eluted directly from the device through centrifugation. For depletion in which the unbound fraction is the sample of interest, the filtration device can be left attached to the column 22 from the beginning of the process.

In certain embodiments, the media column 30 focuses the media, preferably beads, into a column, much like a chromatography column. This creates a packed bed in which fluid is driven through the bed in a way that increases the probability of interaction between the mobile (flow through) and stationary (media) phases. This leads to more efficient binding, washing and elution. Indeed, the number of wash and elution steps can be reduced from three to one each, with minimal or no binding (incubation) time required. Recovered protein shows increased activity when only a single concentration step is used. When binding (incubation) is desirable, the frit 31 is preferably a hydrophobic frit, which inhibits sample flow through the frit, thereby allowing prolonged incubation times until centrifuged to initiate flow. For example, frits comprising hydrophobic material enable incubation of agarose in magnetic bead solutions without dripping, and when subjected to centrifugal G-forces between about 100 and about 700 G, allow passage of filtrate into the receiver tube. Suitable materials include case sintered polypropylene made by Porex Corporation, and a filament extruded polypropylene made by Filtronna Corporation that has been treated with a surface coating such as a fluorinated plasma treatment. Where no binding is desired, such as for buffer exchange and concentration, the media can be omitted from the assembly. The frit (media retention structure) also may be omitted, but since it does not interfere with buffer exchange, it may be left in the device, if desired.

Figure 10:
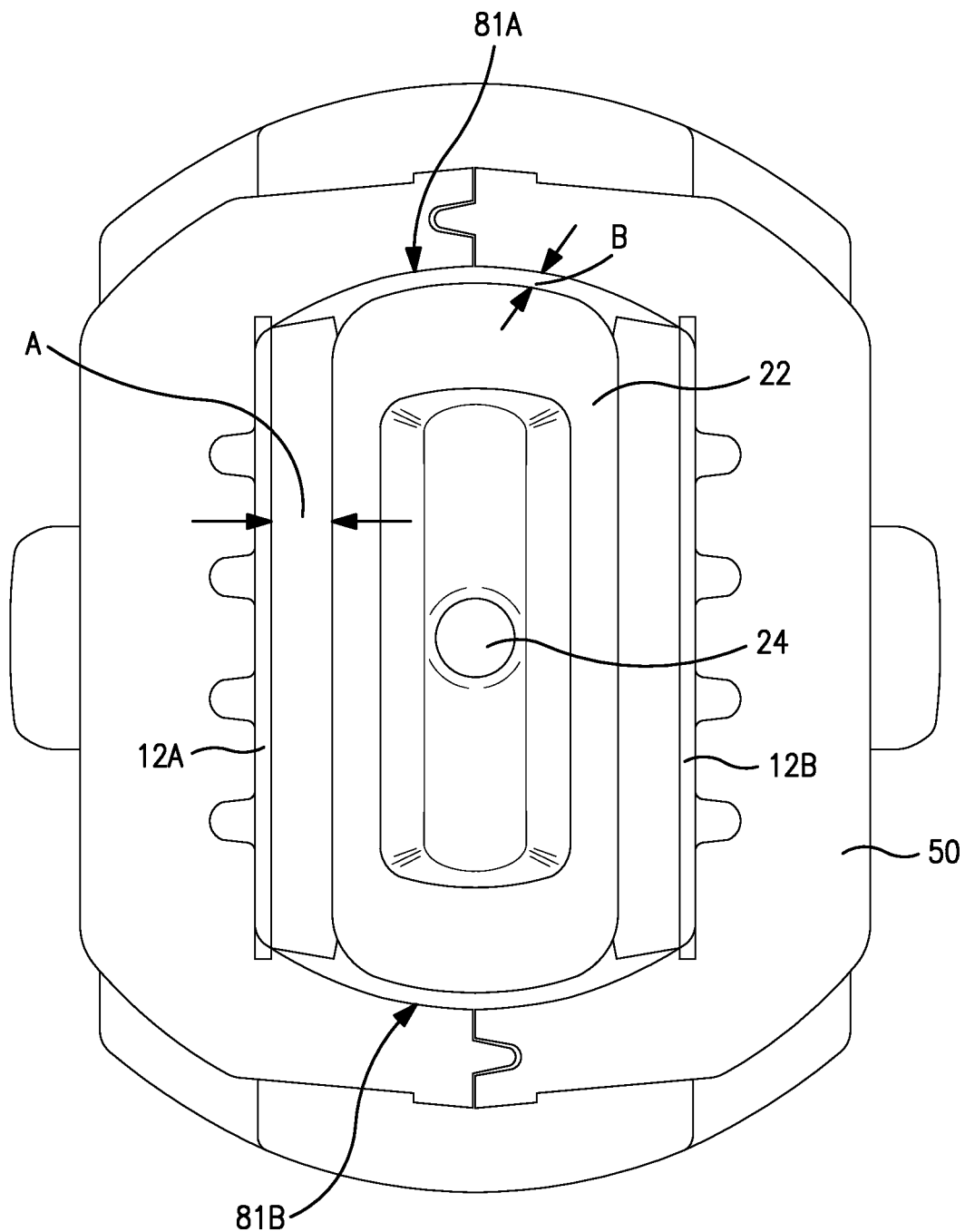
FIG. 10 is a cross-sectional view showing the volume occupied by the exchange member in the filtration device in accordance with certain embodiments.

The finned lower portion of the column 22 allows fresh buffer solution to be exchanged more efficiently than conventional methods. Although the present inventors are not to be bound by any theory, it is believed that it functions based on a diafiltration principle. The matched geometry between the exchange column and the filtration device optimizes the flow of fresh buffer through the system. In accordance with certain embodiments, preferably the fin geometry fills the majority of the unused cavity space inside the filtration device and keeps the sample volume near the outlet hole 24. Since the fresh buffer inside the column 22 and the sample inside the filtration device are in static equilibrium during centrifugation, as the head height of the fresh buffer decreases, the volume of sample leaving the system at any given time is small while there is a large amount of fresh buffer flushing through. This leads to high efficiency. As can be seen in FIG. 10, the offset "A" between the surface of the fin facing membrane 12A (and between the surface of the fin facing membrane 12B) is greater than the offset "B" between the surface of the fin facing the surface of the filtration device where no membrane is present (e.g., at 81A and 81B), so that the fin does not occlude portions of the membrane which could block flow through the membrane. In one embodiment, the offset "A" between the surface of the fin facing each membrane is from about 0.005 inches to about 0.02 inches, preferably 0.020 inches. The offset "B" between the surface of each fin facing the surface of the filtration device where no membrane is present is between about 0.020 inches and about 0.005 inches, preferably about 0.005 inches. Optimally the amount of sample volume is minimized (to optimize the exchange rate) while optimizing the flow characteristics of the membrane. The geometry of the fin helps locate the fluid between the active area of the membranes and the fin, and minimizes the amount of fluid between inactive membrane regions and the fin.

Figure 7:
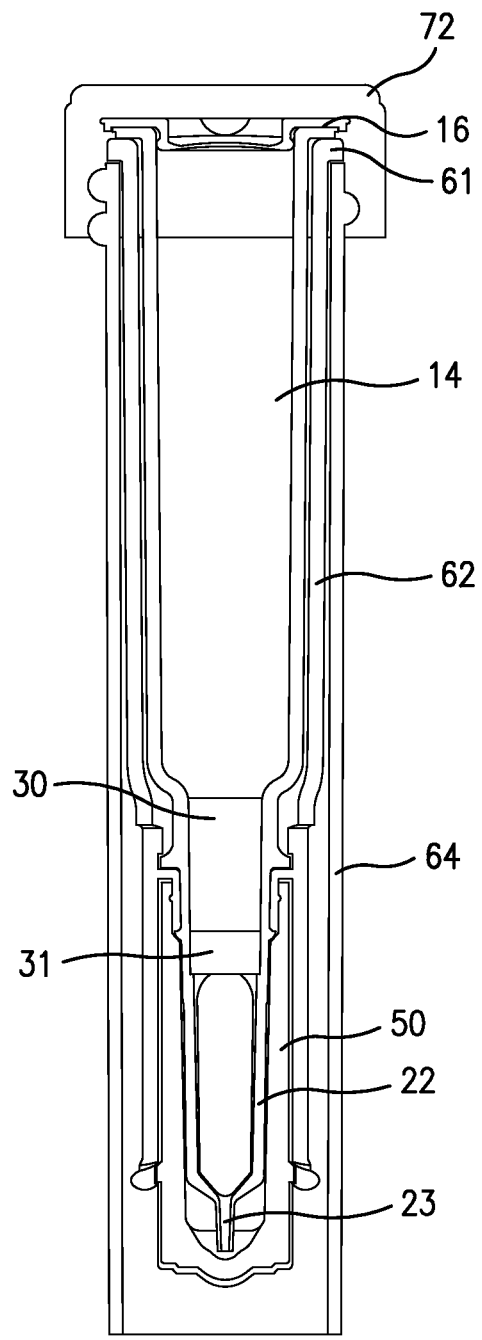
FIG. 7 is a cross-sectional view of an assembly including a reservoir/exchange member, filtration device, assembly holder, centrifuge tube and cap, showing the tip of the reservoir/exchange member positioned in the dead stop volume region of the filtration device, in accordance with certain embodiments.

In addition, by positioning the stem 23 in the dead stop of the filtration device, mixing is enhanced, denature induced aggregation is avoided, and drying out of protein is prevented as fresh buffer is always available via the buffer exchange column. More efficient mixing of buffer solutions is achieved because a control volume is formed in the fluid space of the dead-stop volume. Within this control volume a steady flow system exists. Buffer solution from the reservoir 14 enters, and mixed solution exits through the drain holes 18. Within the control volume the stream of buffer solution exiting the tip 23 creates and maintains a vortex mixing flow. It is this vortex flow that creates more efficient mixing of buffer solutions and sample fluids. As can be seen in FIG. 7, optimal and efficient buffer exchange is achieved when the tip 23 of the exchange device is submerged nearly to the bottom (without contacting the bottom surface which might occlude the exit hole and obstructing out flow) of the sample volume compartment of the filtration device 50 during centrifugation.

Figure 8:
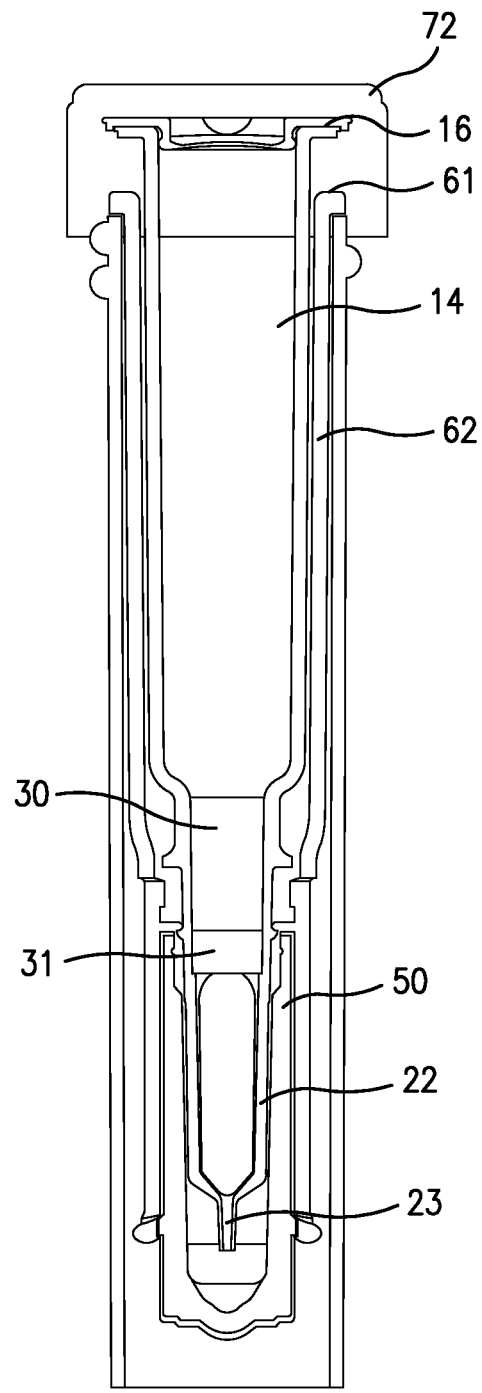
FIG. 8 is a cross-sectional view of an assembly including a reservoir/exchange member, filtration device, assembly holder, centrifuge tube and cap, showing the tip of the reservoir/exchange member lifted out of the dead stop volume region of the filtration device, in accordance with certain embodiments.

In accordance with certain embodiments, there is additional benefit in being able to provide relative movement between the tip 23 and the filtration device 50, such as by lifting the tip 23 of the exchange device out of the sample during centrifugation once buffer exchange has been accomplished, as shown in FIG. 8. This reduces potential sample loss due to the sample clinging to the outer and inner surfaces of the tip due to the surface tension of the materials. Relative movement between the tip and filtration device could be achieved by mechanical means such as a physical stop or by self actuating geometry subject to centrifugal pressure gradient to remove tip engagement with captured target to optimize sample recovery.

Figure 11:
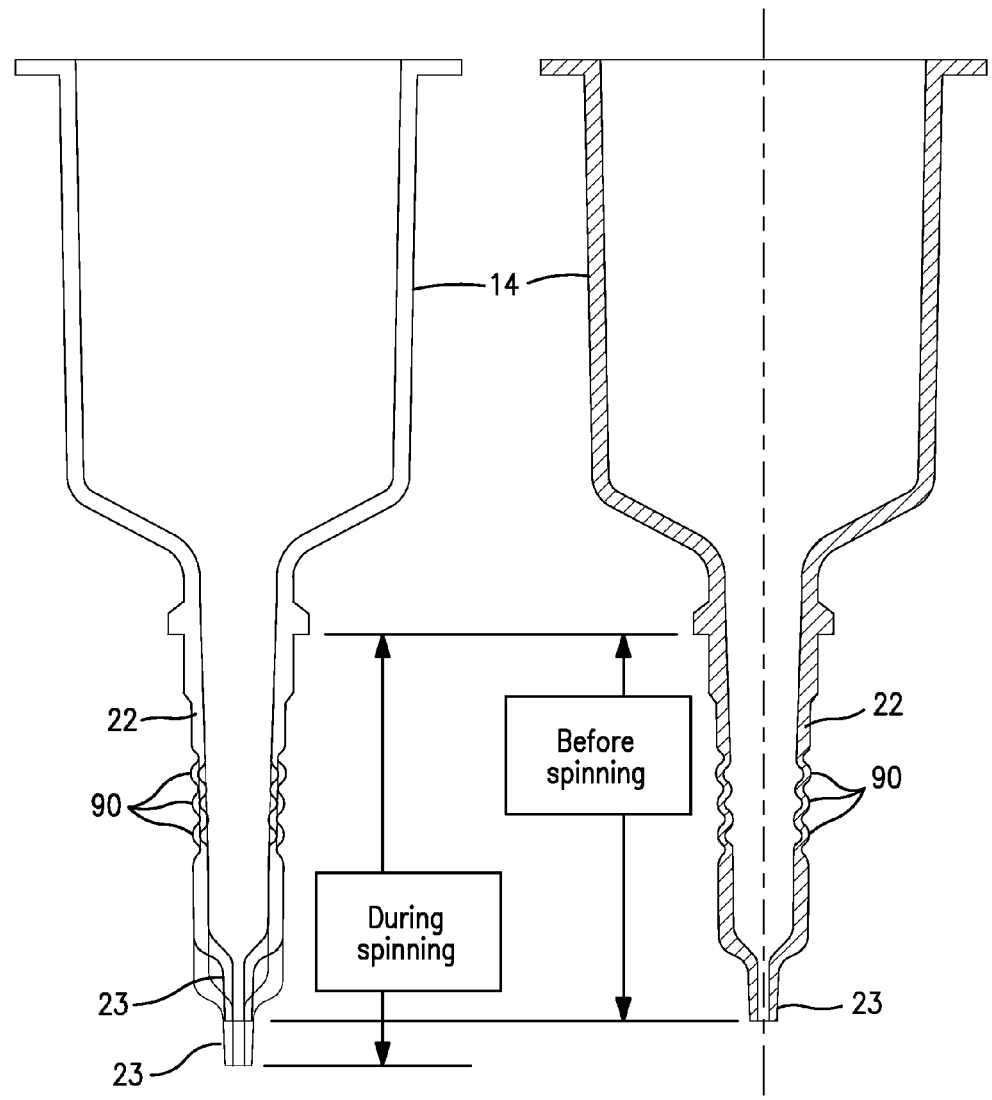
FIG. 11 is a cross-sectional view of a reservoir/exchange member having a portion with convolutions to allow axial movement during centrifugation, in accordance with certain embodiments.

Including a retractable tip design such as that shown in FIG. 11 helps reduce the loss of sample solutions that accumulate on the inner wetted bore and exterior surface of the tip. Initially a concentrated protein sample solution is already located at the bottom of the filtration device 50. Buffer exchange solutions are added to the reservoir 14 and allowed to pass through a frit material and into the filtration device. During centrifugal spin operations, the buffer exchange solution is now into the filtration device 50 where mixing occurs. This mixing enables the salt concentration proteins sample to be diluted by the buffer exchange solution. When spinning has been completed, the end of the tip 23 may still extend into the volume of the concentrated sample. The small amount of sample that wicks into the inner bore of the distal end of the tip and also coats the surface of the exterior wall of the tip can be as much as 5 or 6 µL. The most successful mixing behavior occurs because the distal end of the tip is submerged into the concentrated sample volume.

One option is to perform a secondary spinning operation to move this 5 to 6 µL loss of solution. This may involve stopping the centrifuge and using a mechanical maintenance to lift the entire reservoir out of the sample volume by a distance of 0.100 inch. However, using a secondary spin is undesirable.

Figure 12:
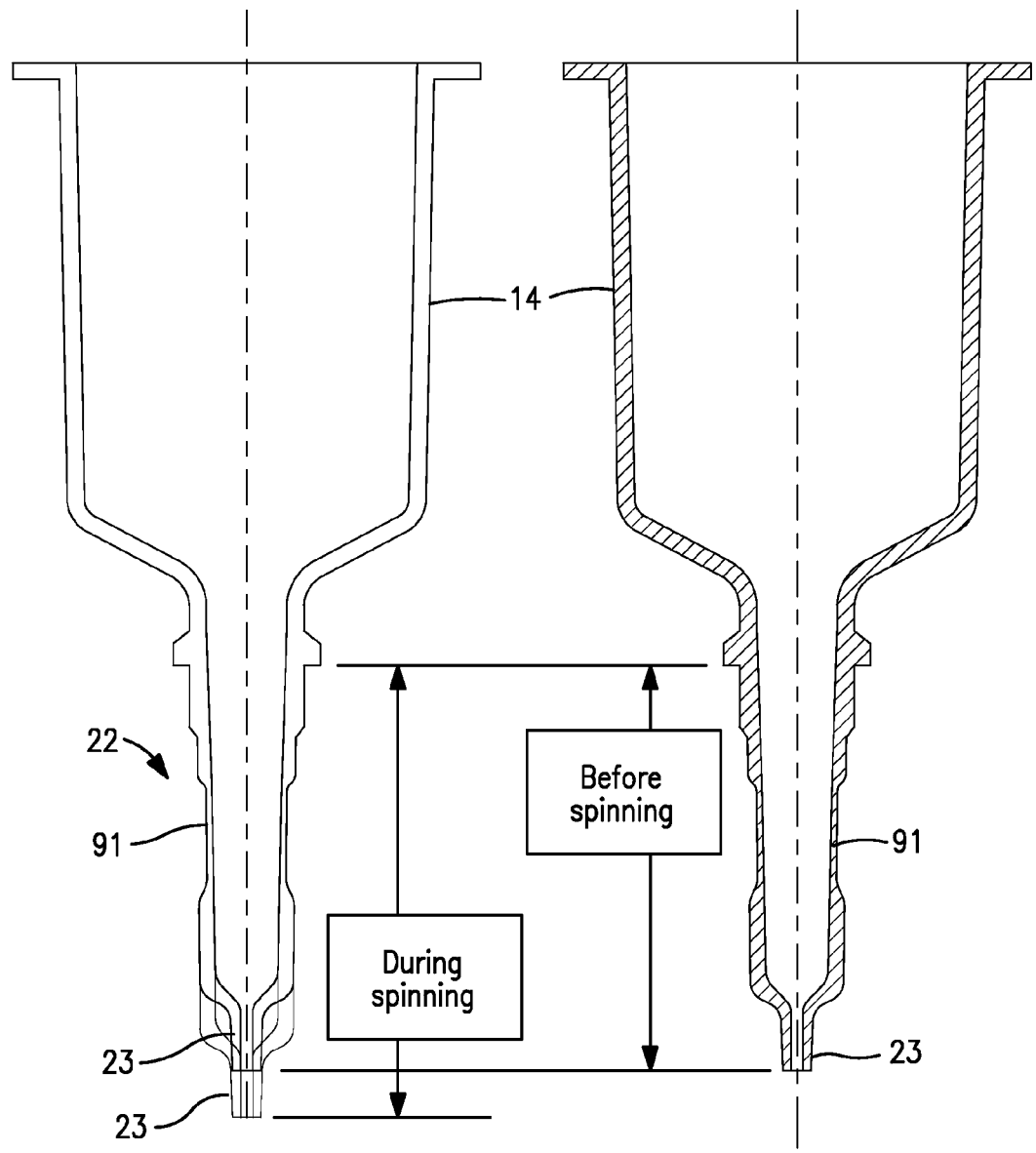
FIG. 12 is a cross-sectional view of a reservoir/exchange member having a thinned-wall portion to allow axial movement during centrifugation, in accordance with certain embodiments.
Figure 13:
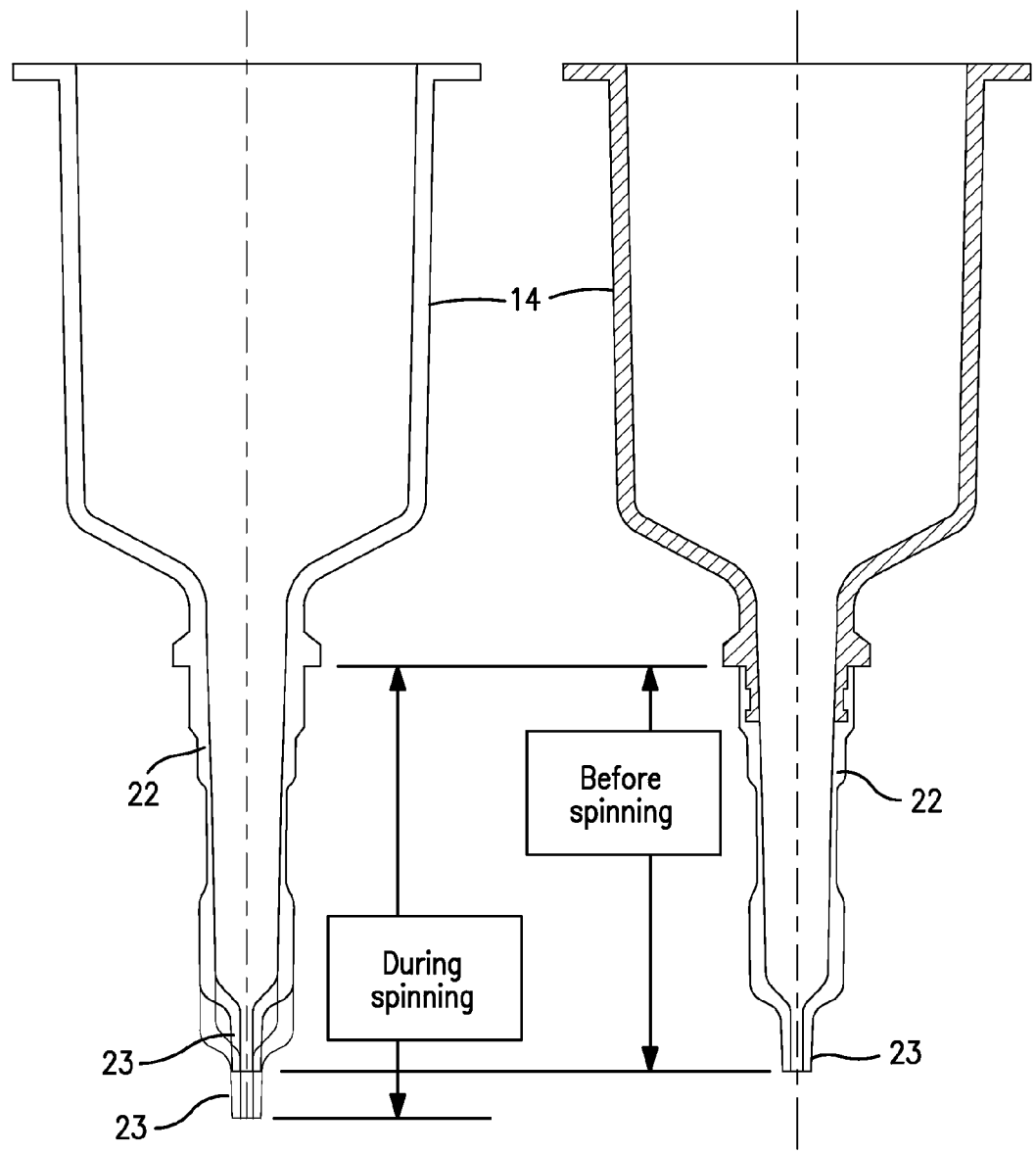
FIG. 13 is a cross-sectional view of a reservoir/exchange member having an over-molded thin-walled portion to allow axial movement during centrifugation, in accordance with certain embodiments.
Figure 14:
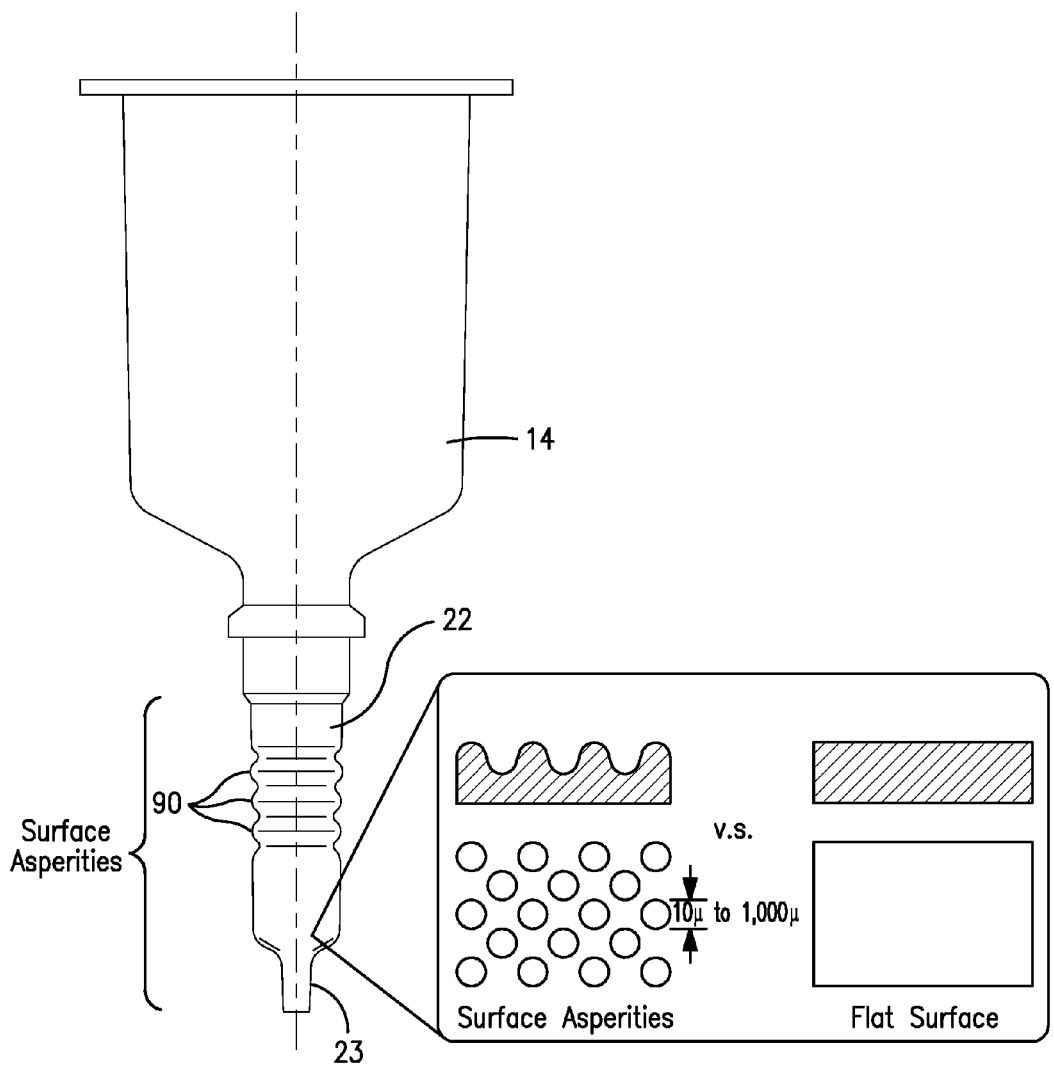
FIG. 14 is a diagrammatic view of a reservoir/exchange member showing the location of molded asperities on the exterior surface of the column, and the exploded detail shows a cross-section the wetted surface and the gas boundary layer.

In contrast, a retractable tip design such as that shown in FIGS. 11-13 enables tips to be drawn into the sample volume due to G-forces when the centrifuge ramps up to spinning speed, and to elastically withdraw from the sample volume when the centrifuge spins down to zero speed. The G-forces pull the tip 23 into the bottom of the sample volume of the filtration device 50, and promote the most effective mixing behavior that is needed to achieve the most effective dilution of buffer solution in a single spin operation. After all the buffer exchange solution has passed through the device, the reduced hydrostatic pressure and reduced G-force during spin down causes the tip 23 to withdraw from the sample volume. The withdrawn tip enables any residual fluid in the inner bore of the tip and the external surface of the tip to be pulled away.

FIG. 11 exemplifies how a single piece reservoir 14 and tip 23 can be configured to have a shortened length prior to spinning, and an increase in length during spinning, in accordance with certain embodiments. The elongation could be achieved by molding or otherwise forming one or more, e.g., one to five (three shown), convolutions 90 into a thinned wall portion of an elastomer material that defines the column 22, so as to achieve an accordion-like configuration. One suitable material is injection molded silicone, which can elongate as much as 50% to 200% without rupturing. Other suitable materials may include polyurethanes and other thermoplastic elastomers, and should have adequate low nonspecific protein binding performance.

If greater stiffness is required in the reservoir portion of the device, elastomer convolutions 90 can be over molded onto the end of a pre-molded reservoir made from polypropylene or an equivalent material.

FIG. 12 shows an example of a more simple design wherein the column 22 includes a straight and thinned wall portion 91. The multiple convolutions have been eliminated from this embodiment. The thinner wall allows the G-forces to extend the axial length of the column 22 during centrifugation. Suitable thin wall thicknesses include between about 0.015 to about 0.040 inches.

FIG. 13 shows an example of an over mold design. The cross-hatched reservoir is pre-molded. The column 22 is over-molded onto the reservoir using a transparent or virtually clear elastomer material, such as liquid injection molded (LIM) silicone, thermoplastic elastomer, or equivalent material. Suitable materials should have non-specific protein binding performance that would not compromise the recovery of the sample proteins of interest.

In accordance with certain embodiments, the reduction of sample hold-up volume can be further improved by reducing the available wetted surface area of the external surface of the feeder tube column 22 and/or tip 23, such as by including a rough and more textured surface on the exterior surface of the column and/or tip. This textured surface may consist of surface asperities (little bumps) that are at least approximately 10μ in diameter and about 10μ high. These surface asperities can be molded into a device using a low surface energy material, such as polypropylene, polyethylene, PTFE or equivalent. These asperities create a surface topography that significantly reduces surface wetting of the device's surface. Only the highest points of the asperities are wetted by the fluid stream and come into contact with the sample fluid. The valleys or troughs remain unwetted and covered by a thin boundary layer of gas, which in this case would typically be air. This significantly reduces sample losses due to wetting behavior (hydrophobic behavior). This also significantly reduces the opportunity for losses that can occur due to nonspecific protein binding of sample fluids. The combination of low surface energy material and asperity surface geometry of create what is known as the lotus effect, which helps reduce sample losses associated with surface hold up of fluids, and undesirable binding of low abundant, high interest protein fractions.

In cases where molding surface asperities into a device may be too difficult or unfeasible, the same surfaces 22 and 23 could be coated with a silicon solvent emulsion to minimize the surface energy of the device, or could be plasma treated.

Where further maximization of sample recovery (particularly with high value sample solutions) is desired, minimizing sample losses due to hold up volumes and nonspecific protein binding is imperative. As the volumes of protein samples become smaller, the undesirable losses of samples due to the hold-up within a device have increased in importance. In accordance with certain embodiments, a diaphragm cap having a biasing member or diaphragm can be included in the device to rescue the loss of sample solutions that accumulate, such as on the wetted bore of the feeder tube. For example, upon completion of centrifugation, small amounts of sample may wick into the inner bore of the distal end of the feeder tube. This small amount of sample or hold-up volume can be as much as 5 or 10 μl. Some or all of this hold-up volume can be evacuated from the inner bore of the device by actuating the biasing member to create pressure in the device and force some or all of this hold-up volume out of the device.

Figure 15:
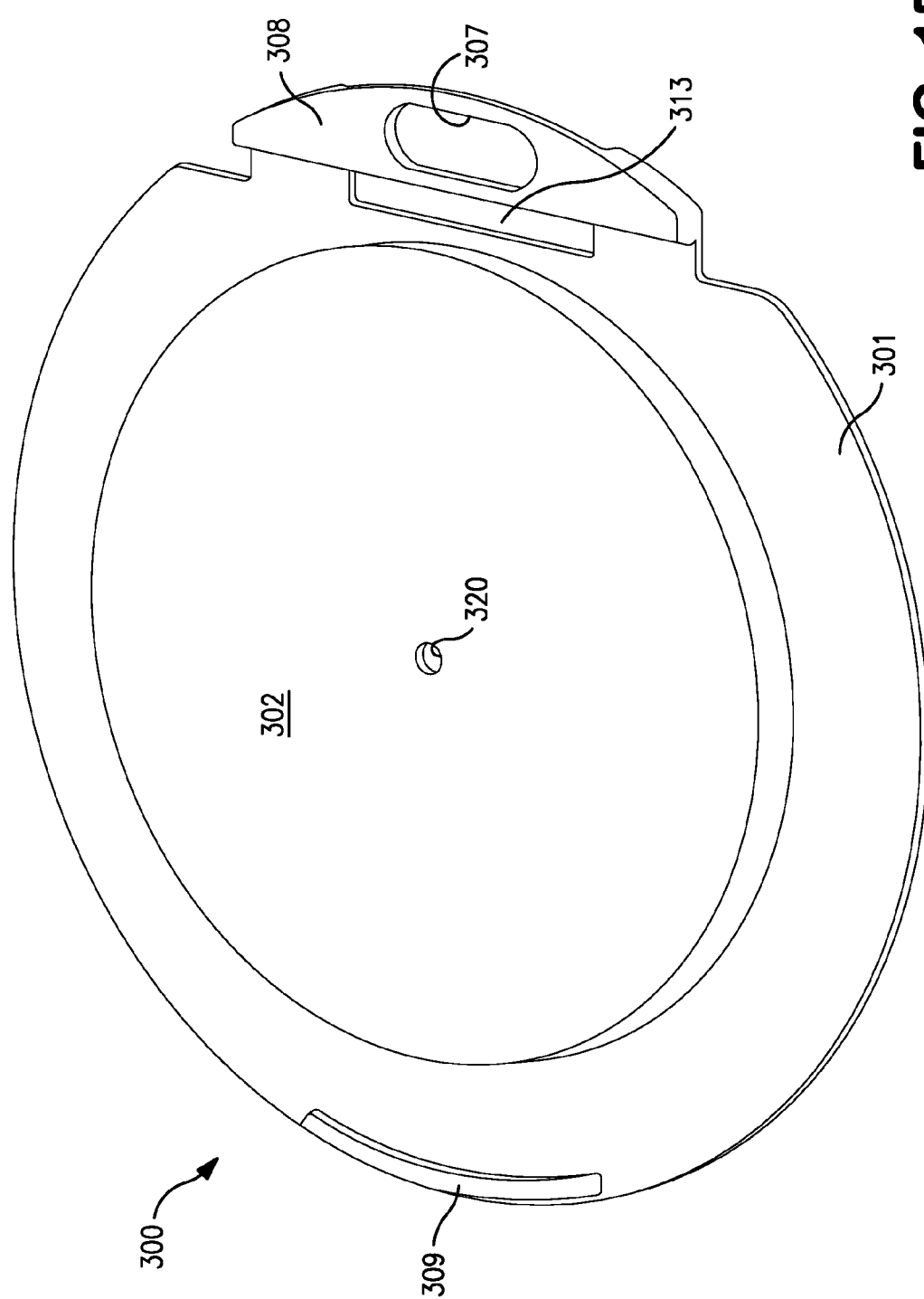
FIG. 15 is a perspective bottom view of a diaphragm cap in accordance with certain embodiments.
Figure 16:
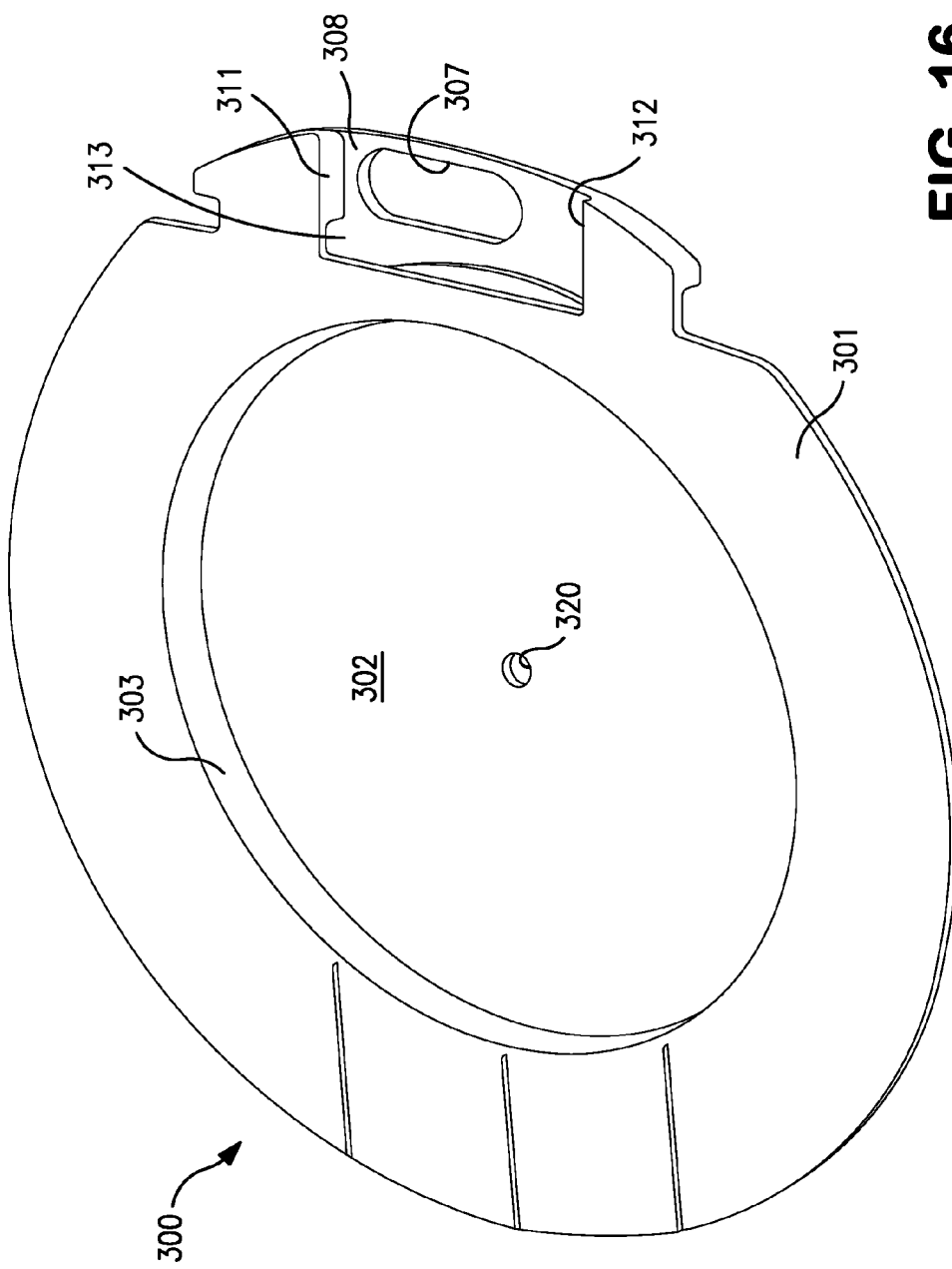
FIG. 16 is a perspective top view of the diaphragm cap of FIG. 15 in accordance with certain embodiments.
Figure 17:
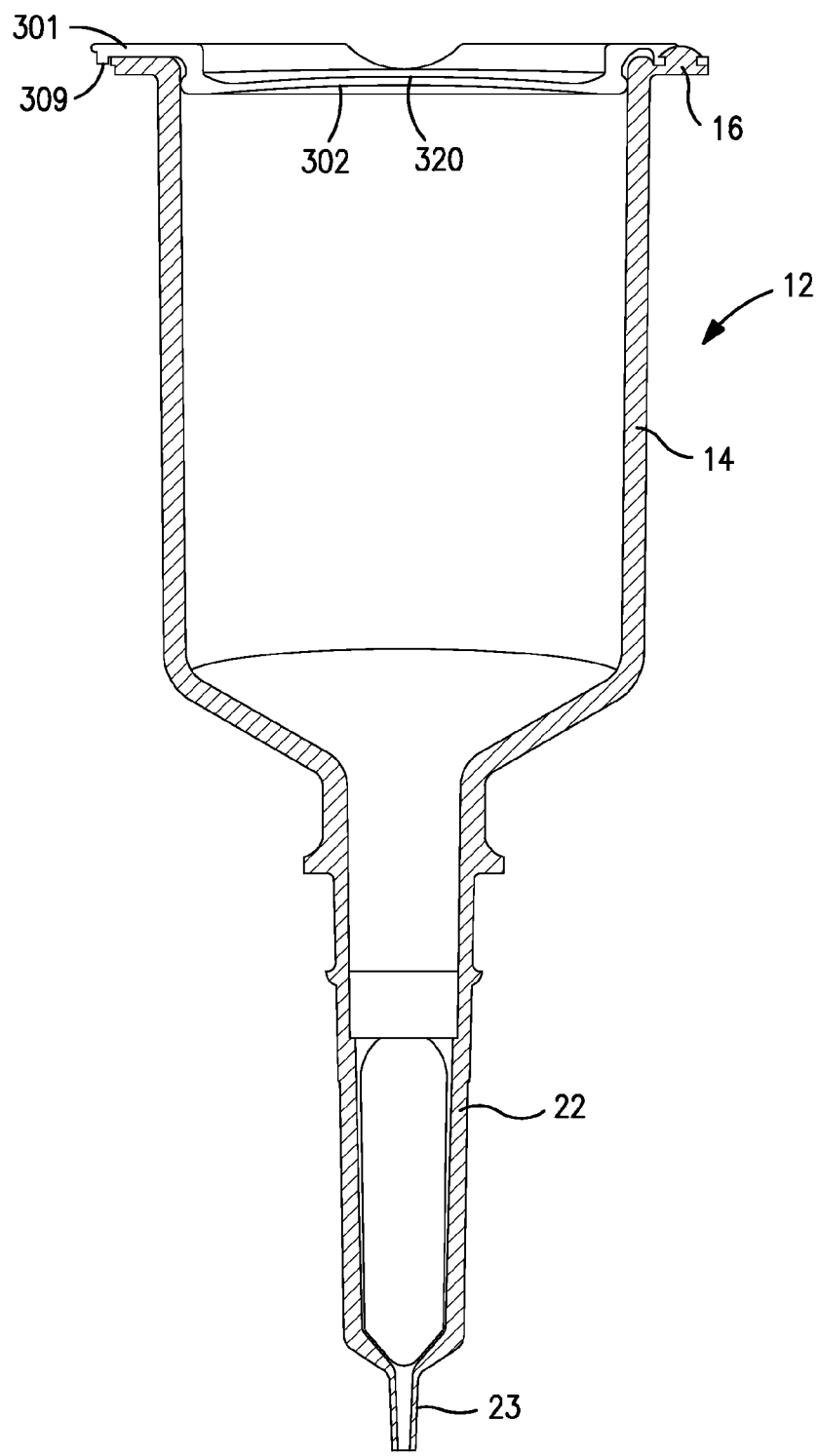
FIG. 17 is a cross-sectional view of a reservoir/exchange member including the diaphragm cap of FIG. 15 in accordance with certain embodiments.

FIGS. 15 and 16 show a diaphragm cap 300 that in certain embodiments can be affixed, preferably hingedly, to the reservoir/exchange member 12. Preferably the diaphragm cap 300 does not interfere with the device cap 72. In certain embodiments, the diaphragm cap 300 includes a perimeter 301 and a biasing region 302 located radially inwardly from the perimeter 301. The biasing region 302 is stepped down from the perimeter 301 via shoulder 303, and includes an aperture 320 to allow air to escape. In certain embodiments, the diaphragm cap 300 is generally circular, with the perimeter 301 being an annular ring, and the biasing region also being circular and having a diameter corresponding to the inner diameter of the inlet (e.g., at the location of the flange 16) of the sample reservoir 14 of the member 12. So dimensioning the biasing region 302 allows the outer perimeter edge of the biasing region 302 to sealingly engage with the inner wall of the member 12 as can be seen in FIG. 17.

Figure 18:
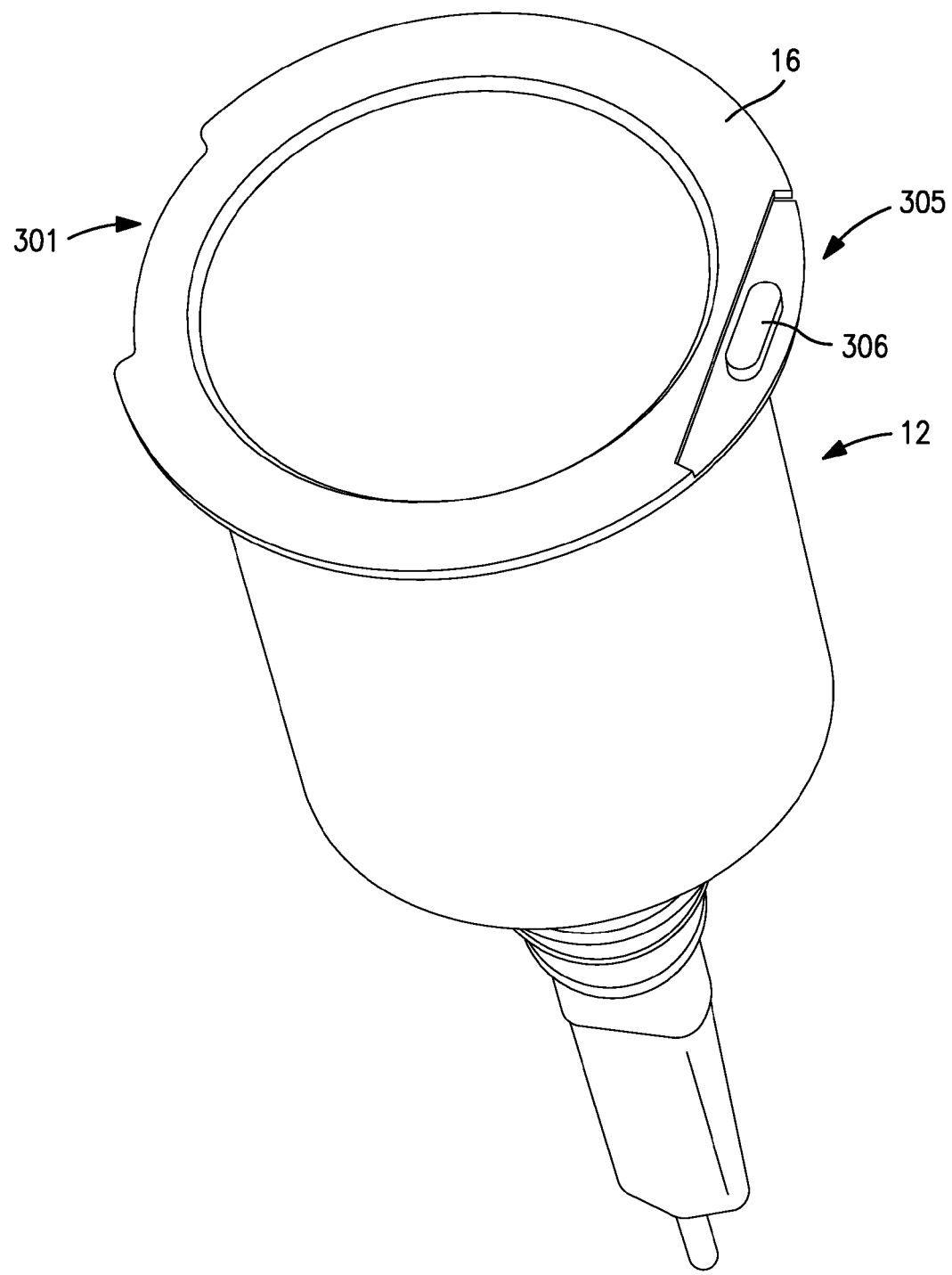
FIG. 18 is a perspective top view of a reservoir/exchange member having a modified flange to accommodate the diaphragm cap of FIG. 15 in accordance with certain embodiments.
Figure 19:
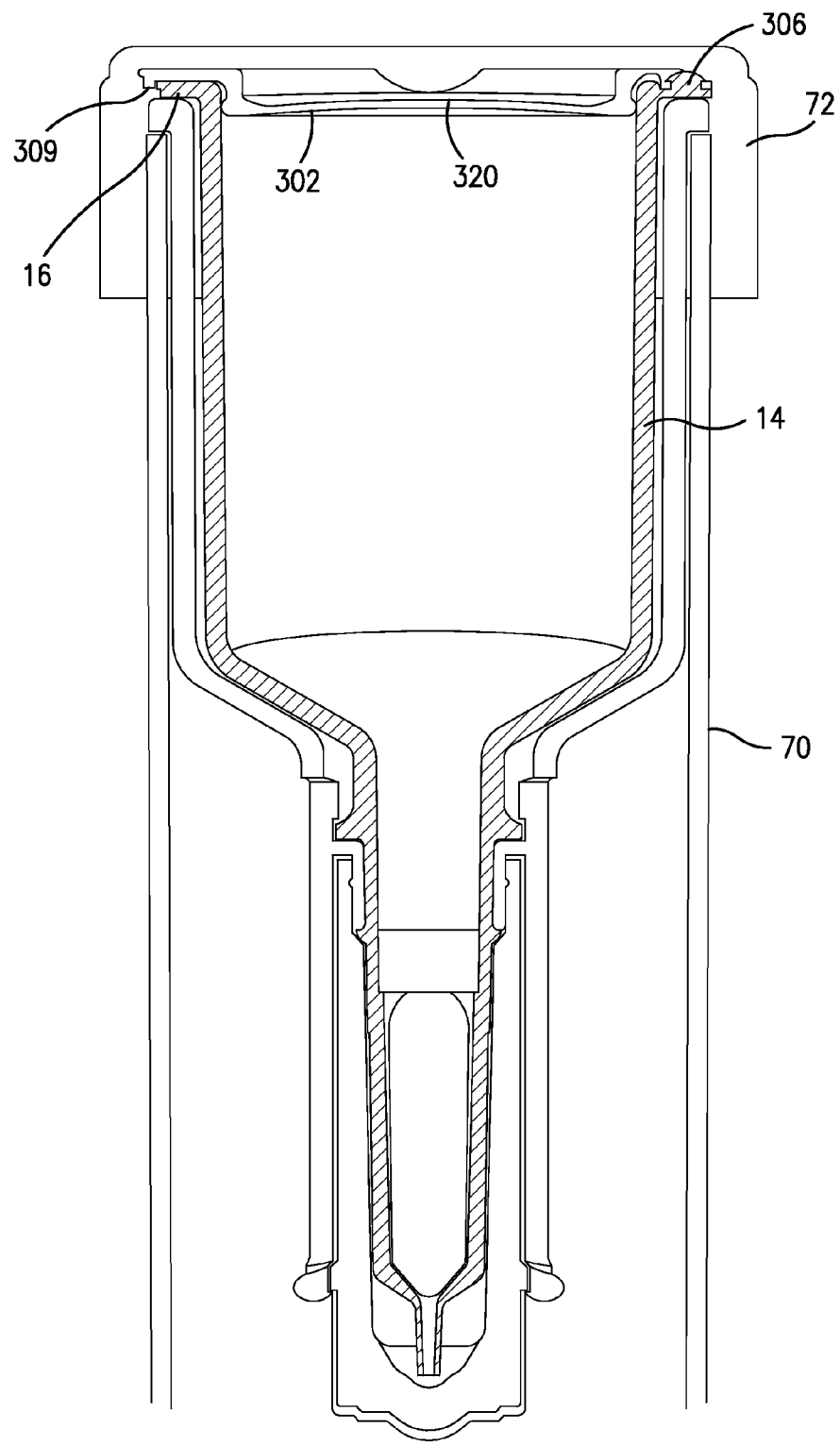
FIG. 19 is a cross-sectional view of an assembly including a diaphragm cap in accordance with certain embodiments.

In certain embodiments, the top surface of the flange 16 of the reservoir/exchange member 12 includes a cap-receiving portion 305, as shown in FIG. 18. The cap-receiving portion is axially recessed slightly from the remainder of the top surface of the flange 16, and includes a button 306 that extends upwardly beyond the remainder of the top surface of the flange 16. The button 306 corresponds in shape to an aperture 307 in the perimeter 301 of the cap 300, which aperture 307 is formed in a perimeter portion 308 that is axially recessed slightly (by the height of shoulders 311, 312) from the remainder of the perimeter 301 (FIG. 16). A second aperture 313 is defined radially inwardly from the perimeter portion 308 as shown in FIGS. 16 and 17. In certain embodiments, the top surface 316 of the button 306 is wider than the width of the aperture 307 (best seen in FIGS. 19 and 21), thereby inhibiting the cap 300 from unintended dislodgement from the reservoir/exchange member 12.

The flange 16 also includes a radially recessed region 307 that in shaped and positioned to cooperate with an axially extending tab 309 on the diaphragm cap 300, to allow the cap 300 to snap onto the member 12. Thus, when the diaphragm cap 300 is in the closed position as shown in FIG. 17, the axially extending tab 309 is positioned in the recessed region 307 of the flange 16. In certain embodiments, the radially recessed region 307 is positioned opposite the cap-receiving portion 305, and the axially extending tab 309 is similarly positioned opposite the perimeter portion 308. The tab 309 and recessed region 307 cooperate to enable single hand manipulation of the diaphragm cap. For example, the user can move the diaphragm cap from its closed position to its open position while holding the device simply by placing the top of their thumb underneath the bottom free end of the tap and lifting it upwards until it releases from the recessed region 307.

Figure 20:
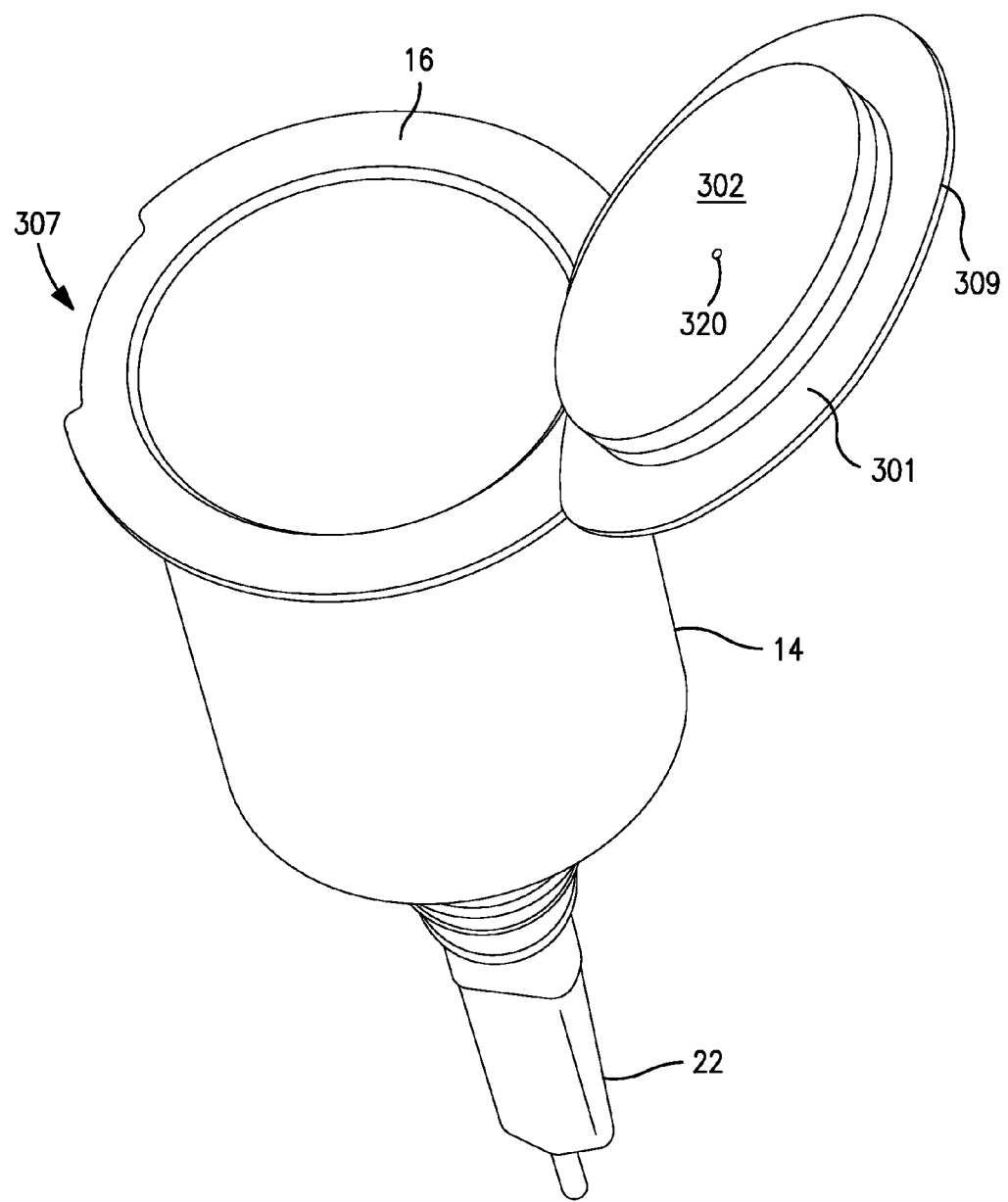
FIG. 20 is a perspective top view of a reservoir/exchange device showing an affixed diaphragm cap in an open position.
Figure 21:
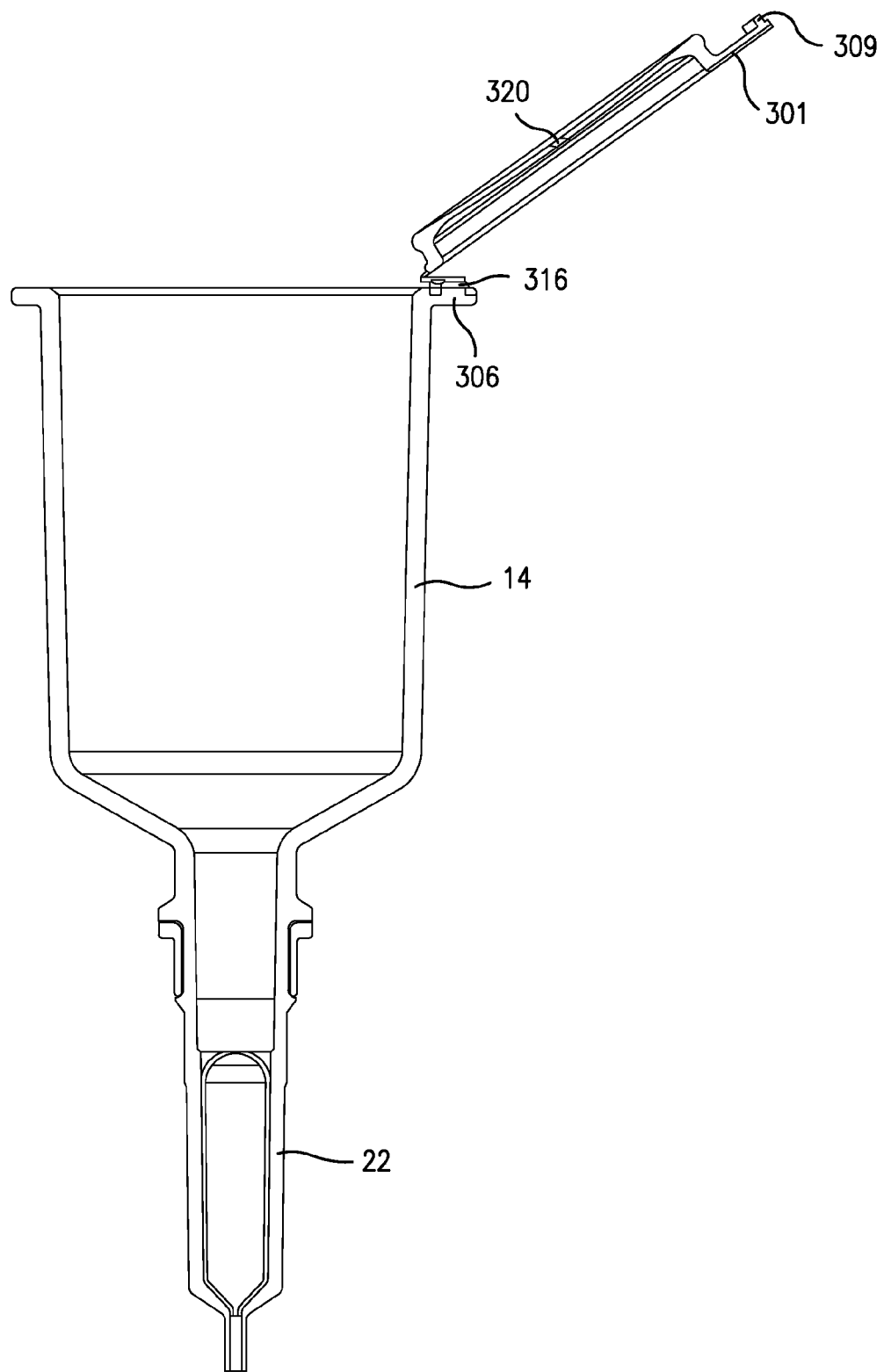
FIG. 21 is a side view of a reservoir/exchange device showing an affixed diaphragm cap in an open position.
Figure 22:
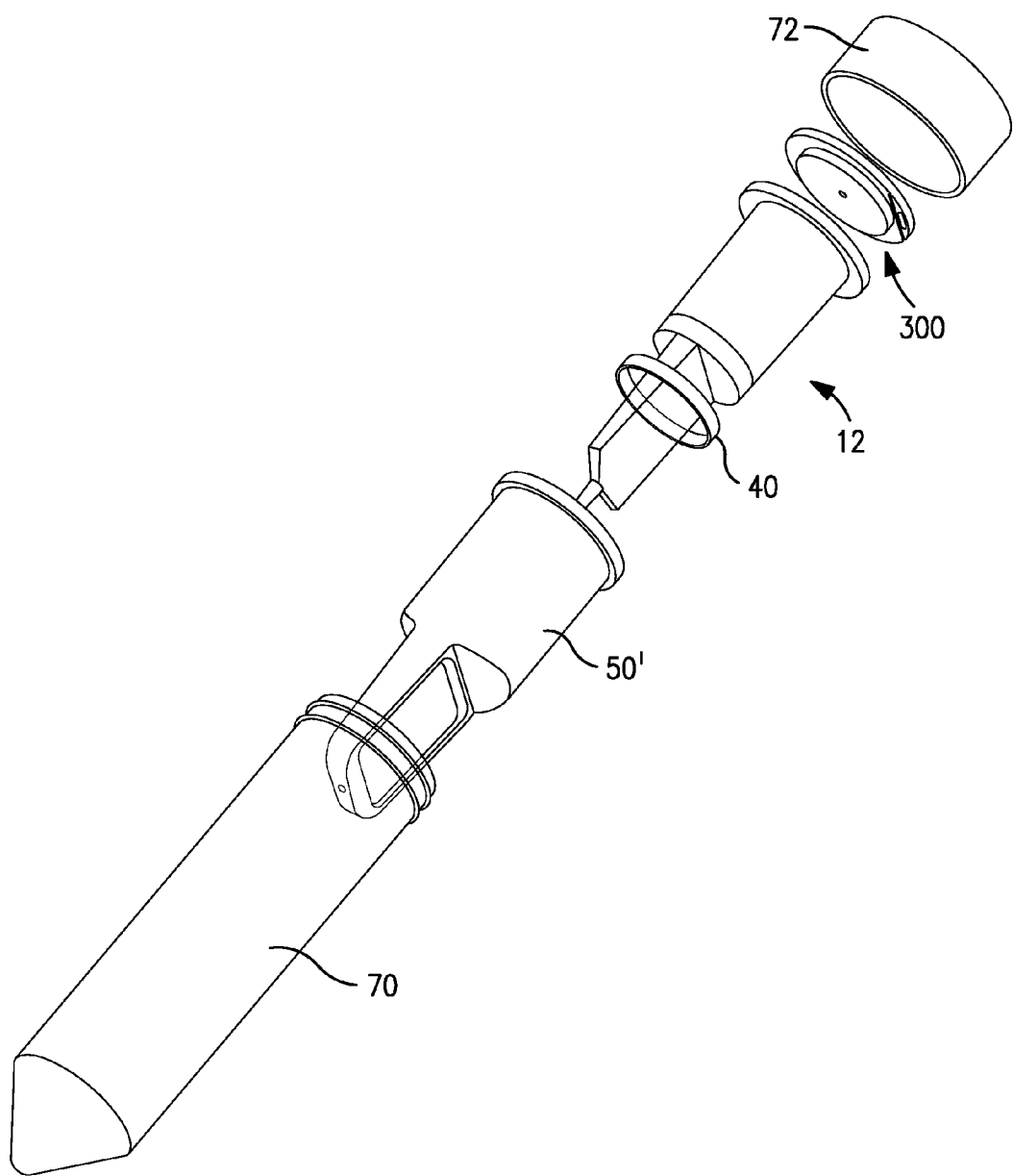
FIG. 22 is an exploded view of a reservoir/exchange device including a diaphragm and a 15 ml filter in accordance with certain embodiments.

FIGS. 20 and 21 illustrate the diaphragm cap 20 in the open position. In the open position, the diaphragm cap 300 remains coupled to the flange 16 via button 306. The aperture 313 defines a radial axis about which the cap 300 can pivot between the open position and the closed position, thus defining a living hinge. FIG. 22 shows an exploded view of an embodiment including a larger filter, such as a 15 ml filter 50'. In the embodiment shown, an assembly holder is not used, although one could be present.

The biasing member or diaphragm 302 is made of a deformable flexible material, and thus easily can be deflected axially, such as by the user's index finger, when the diaphragm cap is in place in its closed position. Actuating the member 302 in this way creates a force within the device which evacuates hold-up fluid in the inner cavity of the feeder tube and distal tube and thus reduces or eliminates hold-up volume.

The diaphragm cap 300 allows for centrifugation of the device assembly with or without the threaded cap 70 in place.

The diaphragm or biasing member can be elastomeric or thermo-formed.

Example 1

Affinity Depletion

In this protocol, the major contaminants of the sample are selectively bound to the media while the components of interest remain in solution. Upon completion of the binding step, the solution is harvested for further analysis.

Figure 9:
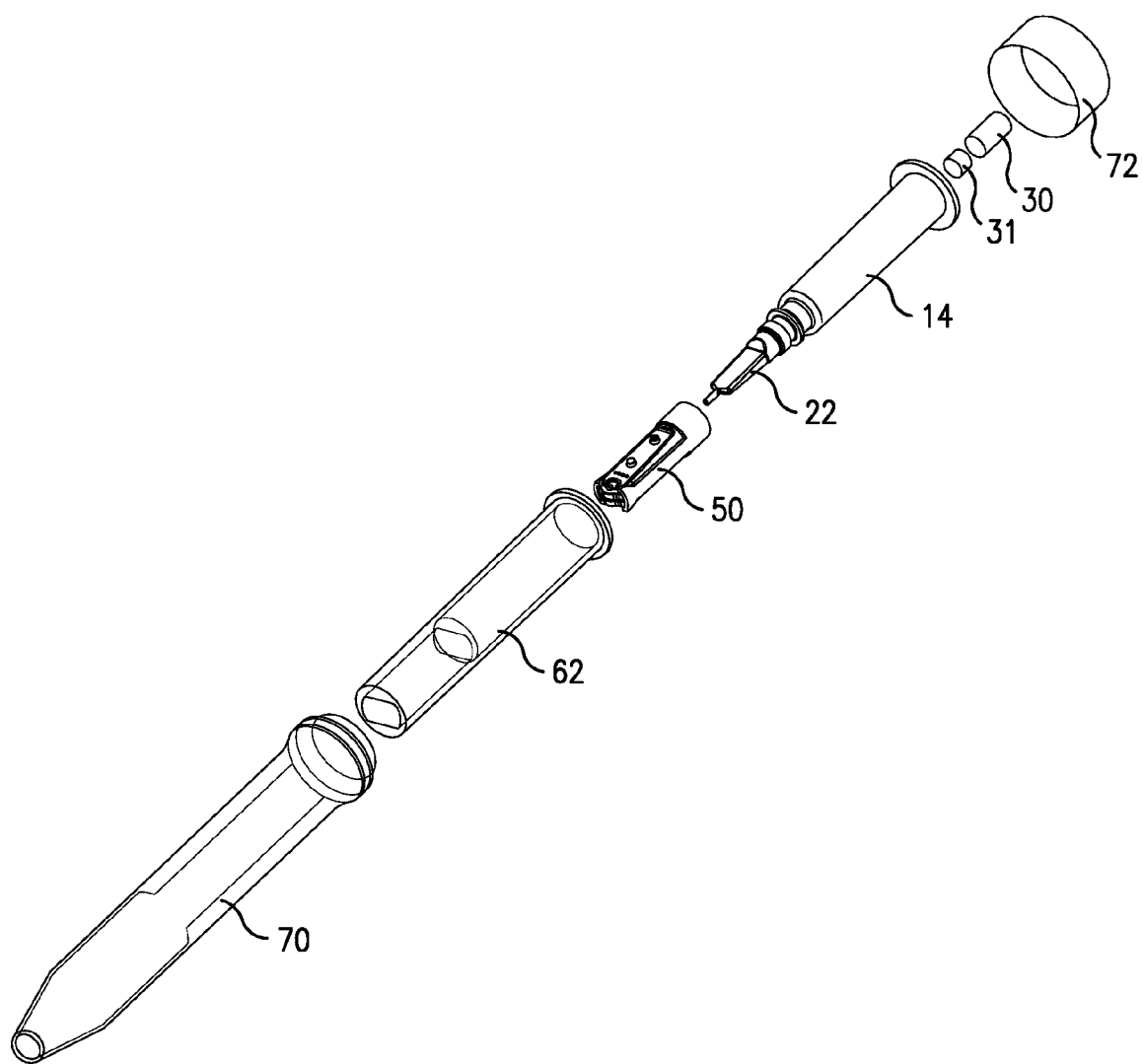
FIG. 9 is an exploded perspective view of a bind, wash, elute and concentration device in accordance with certain embodiments.

Beads that bind both albumin and IgG are added to the fully assembled bind, wash, elute and concentrate (BWEC) device (e.g., FIG. 9. A serum sample is then added and allowed to interact with the beads which then selectively remove the albumin and IgG from the sample by adsorbing them onto the surface of the beads via interaction with immobilized anti-albumin antibody and immobilized protein A. After the incubation step, the beads are separated from the unbound components in the liquid by centrifugation. The beads are held back by the frit in the BWEC device while the solution containing the analytes and biomarkers of interest passes to the chamber below. That chamber may simply be the test tube or it may be a filtration device such as an Amicon Ultra-0.5 centrifugal filtration unit, which provides the benefit that the protein biomarkers in the sample may be concentrated in the same centrifugal step as the bead removal. This is especially significant for affinity depletion as serum samples typically require a 10 fold dilution prior to bead incubation because the albumin and IgG to be removed are at very high concentration and need to contact a large volume of beads to effect complete removal. Once the abundant proteins are removed from the diluted samples, the remaining targets of interest typically need to be concentrated. Thus the coupling of the bead removal/separation and sample concentration steps reduces the required handling in the workflow.

Example 2

Affinity Purification

Set forth herein is a typical example of how affinity beads are used to purify an analyte of interest. In this case, the beads are used to selectively bind the target, the contaminants are washed away and then the analyte of interest is eluted from the beads by changing the buffer system.

Immobilized metal affinity chromatography (IMAC) beads which are charged with copper are loaded into the BWEC device along with a sample that contains a fusion protein linked to the 6×His affinity purification tag. It is the 6×His tag that is known to bind to the copper charged IMAC beads (a.k.a. his tag beads). Once binding is complete, the device is centrifuged to remove the contaminants that remain in solution while the beads are retained by the frit in the device. The beads may be washed with additional loading buffer to obtain a cleaner purification. However, the initial separation and washes are done without the filtration device (e.g., without an Amicon Ultra-0.5 ml device) and the unbound solution and washes are collected as waste in the bottom of the centrifuge tube. Once the washes are complete, the filtration device (e.g., an Amicon Ultra-0.5 device) is attached to the outlet of the BWEC device and an elution buffer which dissociates the target from the beads is added. The purified target is then collected and concentrated in the filtration device in a single spin without requiring additional transfer steps.

Example 3

Buffer Exchange

Examples 1 and 2 only take advantage of the bead handling functionality of the BWEC device. Now described is the buffer exchange capability. Ultra filtration devices have long been used for buffer exchange. This is accomplished by simply concentrating the sample (e.g. 10 fold from 500 μl down to 50 μl) and then diluting with the new buffer back to the original volume. In a single step this would give rise to roughly a 10 fold or 90% buffer exchange. This is typically insufficient with an optima on the order of a 99.9% buffer exchange, which would require three separate spins with a typical ultrafiltration device such as the Amicon Ultra-0.5 device. Furthermore, if one were to simply dilute the sample with the full volume, 1.5 ml in this example, in a single spin, it would not be as effective (96.7%) as three spins at 0.5 ml each (99.9%). Although 96.7% may seem to be close to 99.9%, there is indeed 33 times more remaining buffer in the sample which was exchange to 96.7%. The key to a successful single spin is to meter the new buffer into the sample slowly with mixing rather than a single large dilution.

A protein/DNA sample containing azide or some other undesirable buffer or salt is first added to the fully assembled device (BWEC plus the filtration device, e.g., an Amicon Ultra-0.5). It is then centrifuged and concentrated to 50 ul. Next, 1.5 ml of the new buffer is added to the device and it is centrifuged again. The device slowly meters the new buffer into the sample and flushes out the old undesirable buffer, leaving the concentrated sample in the new buffer.

Example 4

Combination Affinity Purification with Buffer Exchange

Where an affinity purified or depleted sample also requires buffer exchange in addition to concentration, this may be accomplished by simply combining the steps of purification with buffer exchange.

IMAC beads are loaded into the BWEC device along with a sample that contains a fusion protein linked to the 6X His. Once binding is complete, the device is centrifuged to remove the contaminants that remain in solution while the beads are retained by the frit in the device. The beads may be washed with additional loading buffer to get a cleaner purification. Once the washes are complete, the filtration device (e.g., an Amicon Ultra-0.5 device) is attached to the outlet of the BWEC device and an elution buffer which dissociates the target from the beads is added. The purified target is then collected and concentrated in the filtration device in a single spin without requiring additional transfer steps. To remove imidazole, which is typically used in the elution buffer, one may add 1.5 ml of PBS to the device and spin again. The PBS will have no impact on the beads and vice versa. The PBS will be slowly metered into the previously eluted sample, flushing out the imidazole, replacing it with PBS.

Example 5

Hold-Up Volumes

Figure 26:
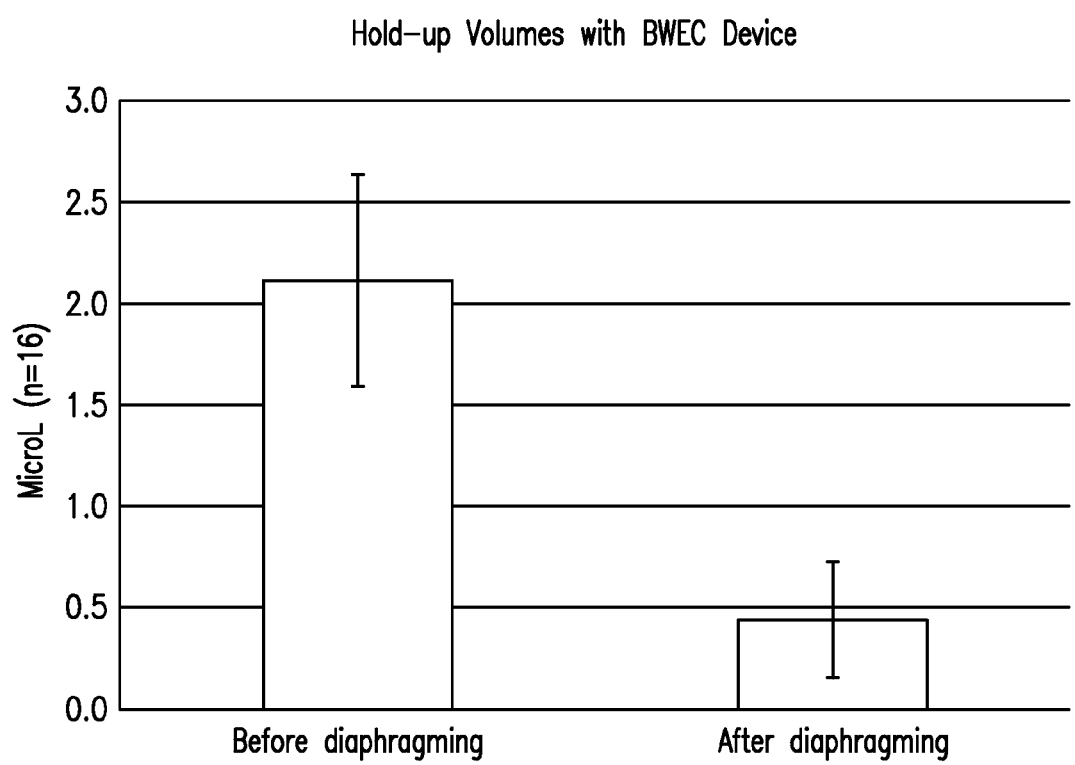
FIG. 26 is a graph showing hold-up volumes of devices with and without diaphragms in accordance with certain embodiments.

Hold-up volumes were evaluated with bind-wash-elute-concentrate (BWEC) devices and diaphragm caps. The devices were pre-washed with 1.5 ml BSA (1 mg/ml PBS) at 4000×g for 2 minutes, and then 0.5 ml BSA (1 mg/ml PBS) was added to each of the devices after assembling with a 0.5 µm filter device (AMICON ULTRA 0.5 ml 10K, available from EMD Millipore Corporation), followed by centrifugation for 15 minutes at 4000×g. The hold-up volumes were calculated by weight difference of the devices before and after actuating the diaphragm. The results are shown in FIG. 26, and demonstrate that actuation of the diaphragm results in the recovery of more than 1.5 µl of sample compared to no diaphragm.

Example 6

Figure 27:
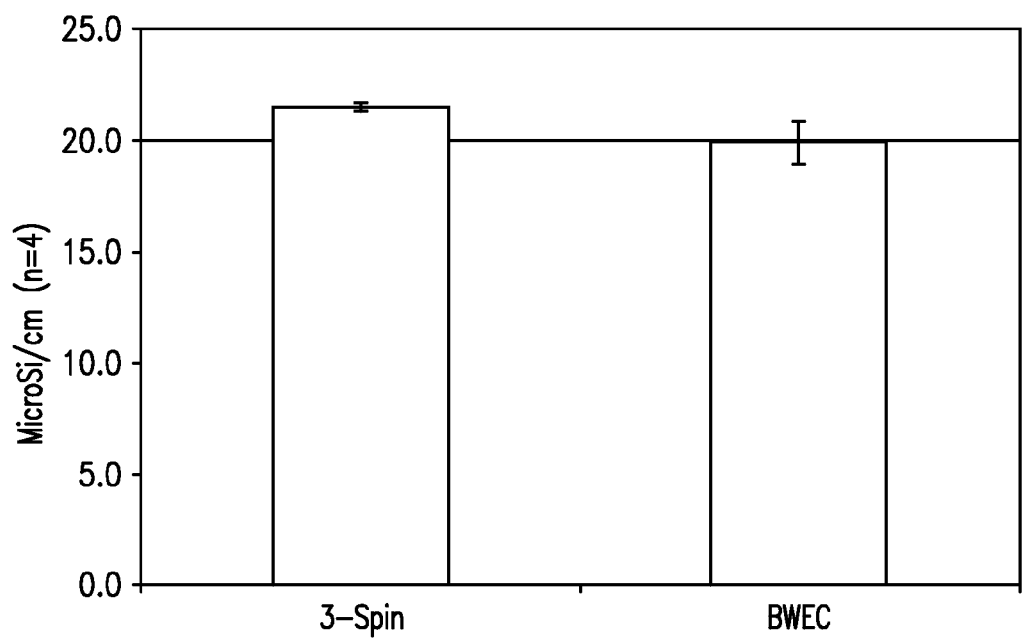
FIG. 27 is a graph comparing a 3-spin procedure to a bind-wash-elute procedure in accordance with certain embodiments.

Bind-wash-elute (BWE) devices were evaluated on buffer exchange. 50 µl of 10 mM Tris, pH 7.5, 1 M NaCl was distributed to a filter device (AMICON ULTRA 0.5 ml 10K, available from EMD Millipore Corporation) and assembled into exchange tubes and centrifuged at 4000×g for 15 minutes after adding 1.5 ml of 10 mM Tris, pH 7.5 to the exchange tube. The retentates were collected by reverse spin for 2 minutes at 1000×g and the final volume was adjusted to 100 µl with 10 mM Tris. Conductivities were measured after adding 4.9 ml Milli-Q water. For the 3-spin control, buffer exchange was carried out by three consecutive washes with 0.5 ml. FIG. 27 shows that bind-wash-elute performed equivalent to the 3-spin method despite only a single spin.

What is claimed is:

1. A sample preparation device, comprising a reservoir/exchange member having a sample reservoir, a plurality of columns extending axially from said reservoir and having an outlet spaced from and in fluid communication with said sample reservoir, and a plurality of filtration devices attached to said reservoir/exchange member via a respective one of said plurality of columns, each said filtration device comprising a filtrate chamber, one or more spaced membranes sealingly positioned between said sample reservoir and said filtrate chamber, a retentate chamber defining a dead-stop volume below said membranes, wherein each said outlet of each said column is positioned in the dead stop volume of its respective filtration device.

2. The sample preparation device of claim 1, wherein each said outlet comprises an aperture on a stem extending axially from a respective one of said columns.

3. The sample preparation device of claim 2, wherein each said stem is axially extendable and axially retractable within said dead stop volume.

4. The sample preparation device of claim 3, wherein each said stem is fixed at one end by said reservoir and comprises an elastomer overmolded portion that is axially extendable and axially retractable within said dead stop volume.

5. The sample preparation device of claim 3, wherein each said stem comprises one or more convolutions that allow it to be axially extendable and axially retractable within said dead stop volume.

6. The sample preparation device of claim 1, wherein each said filtration device comprises two spaced membranes, and has a volume between said spaced membranes, and wherein said column comprises a chamber shaped to occupy said volume such that said chamber is offset from each of said membranes.

7. The sample preparation device of claim 6, wherein each said chamber of each said column tapers radially inwardly towards said outlet.

8. The sample preparation device of claim 1, further comprising a diaphragm cap comprising a biasing member positioned in said reservoir/exchange member.

9. The sample preparation device of claim 1, wherein each said column comprises chromatography media.

10. The sample preparation device of claim 1, wherein each said column comprises a frit.

11. The sample preparation device of claim 10, wherein each said frit comprises hydrophobic material.

12. The sample preparation device of claim 1, wherein each said column is removable from said reservoir/exchange member.

13. The sample preparation device of claim 1, wherein each said column is attached to said reservoir/exchange member by a threaded connection.

* * * * *